(12) United States Patent
Keil et al.

(10) Patent No.: US 8,852,472 B2
(45) Date of Patent: *Oct. 7, 2014

(54) COATED LIPID COMPLEXES AND THEIR USE

(75) Inventors: Oliver Keil, Glienicke (DE); Jörg Kaufmann, Berlin (DE)

(73) Assignee: Silence Therapeutics GmbH, Berlin (DE)

( * ) Notice: Subject to any disclaimer, the term of this patent is extended or adjusted under 35 U.S.C. 154(b) by 2079 days.

This patent is subject to a terminal disclaimer.

(21) Appl. No.: 11/722,948

(22) PCT Filed: Dec. 27, 2005

(86) PCT No.: PCT/EP2005/014074
§ 371 (c)(1),
(2), (4) Date: Jan. 11, 2008

(87) PCT Pub. No.: WO2006/069782
PCT Pub. Date: Jul. 6, 2006

(65) Prior Publication Data
US 2010/0062967 A1    Mar. 11, 2010

(30) Foreign Application Priority Data
Dec. 27, 2004   (EP) .................. 04030846

(51) Int. Cl.
| | | |
|---|---|---|
| *A61J 3/07* | (2006.01) | |
| *A61K 51/00* | (2006.01) | |
| *A61M 36/14* | (2006.01) | |
| *B32B 5/16* | (2006.01) | |
| *B32B 21/02* | (2006.01) | |
| *C12N 15/88* | (2006.01) | |
| *A61K 47/48* | (2006.01) | |
| *A61K 48/00* | (2006.01) | |

(52) U.S. Cl.
CPC ..... *A61K 47/48046* (2013.01); *A61K 47/48815* (2013.01); *A61K 48/0033* (2013.01); *Y10S 977/907* (2013.01)

USPC .......... 264/4; 424/1.21; 428/402.2; 435/458; 977/907

(58) Field of Classification Search
None
See application file for complete search history.

(56) References Cited

U.S. PATENT DOCUMENTS

| | | | | |
|---|---|---|---|---|
| 5,820,873 | A  * | 10/1998 | Choi et al. | 424/283.1 |
| 6,358,523 | B1 | 3/2002 | Safinya et al. | |
| 6,586,410 | B1 | 7/2003 | Wheeler et al. | |
| 7,015,040 | B2 * | 3/2006 | Wolff et al. | 435/458 |
| 7,196,145 | B2 * | 3/2007 | Ignatious | 525/523 |
| 2003/0073640 | A1 * | 4/2003 | Beigelman et al. | 514/19 |

FOREIGN PATENT DOCUMENTS

| | | |
|---|---|---|
| WO | WO 96/10392 | 4/1996 |
| WO | WO 98/44909 | 10/1998 |
| WO | WO 98/51285 | 11/1998 |
| WO | WO 99/04819 | 2/1999 |
| WO | WO 01/05374 | 1/2001 |
| WO | WO 01/80900 | 11/2001 |
| WO | WO 02/34236 | 5/2002 |
| WO | WO 2004/012680 | 2/2004 |
| WO | WO 2005/105152 | 11/2005 |
| WO | WO 2006/053646 | 5/2006 |
| WO | WO 2006/074546 | 7/2006 |

OTHER PUBLICATIONS

International Search Report dated Dec. 27, 2004.

* cited by examiner

*Primary Examiner* — Robert M Kelly
(74) *Attorney, Agent, or Firm* — Saliwanchik, Lloyd & Eisenschenk

(57) ABSTRACT

The present invention is related to a lipid composition comprising at least a first lipid component, at least a first helper lipid, and a shielding compound which is removable from the lipid composition under in vivo conditions.

48 Claims, 16 Drawing Sheets general structure of compounds according to the present invention:

Figure 2
starting material: oleyl amine
Fluka technical grade ≥ 70% (GC)
~30% amines with different alkyl chains
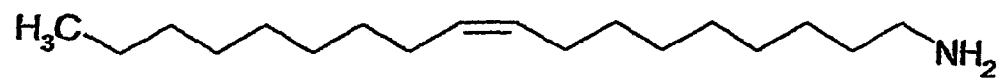
+
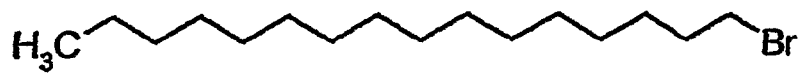
1-bromohexadecane (palmityl bromide)
30 min,
100-120°C    (83%)
neat
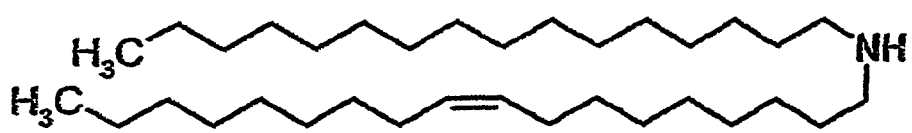
*N*-oleyl-palmityl amine tri-Boc-γ-carbamidino-α,γ-diaminobutyric acid

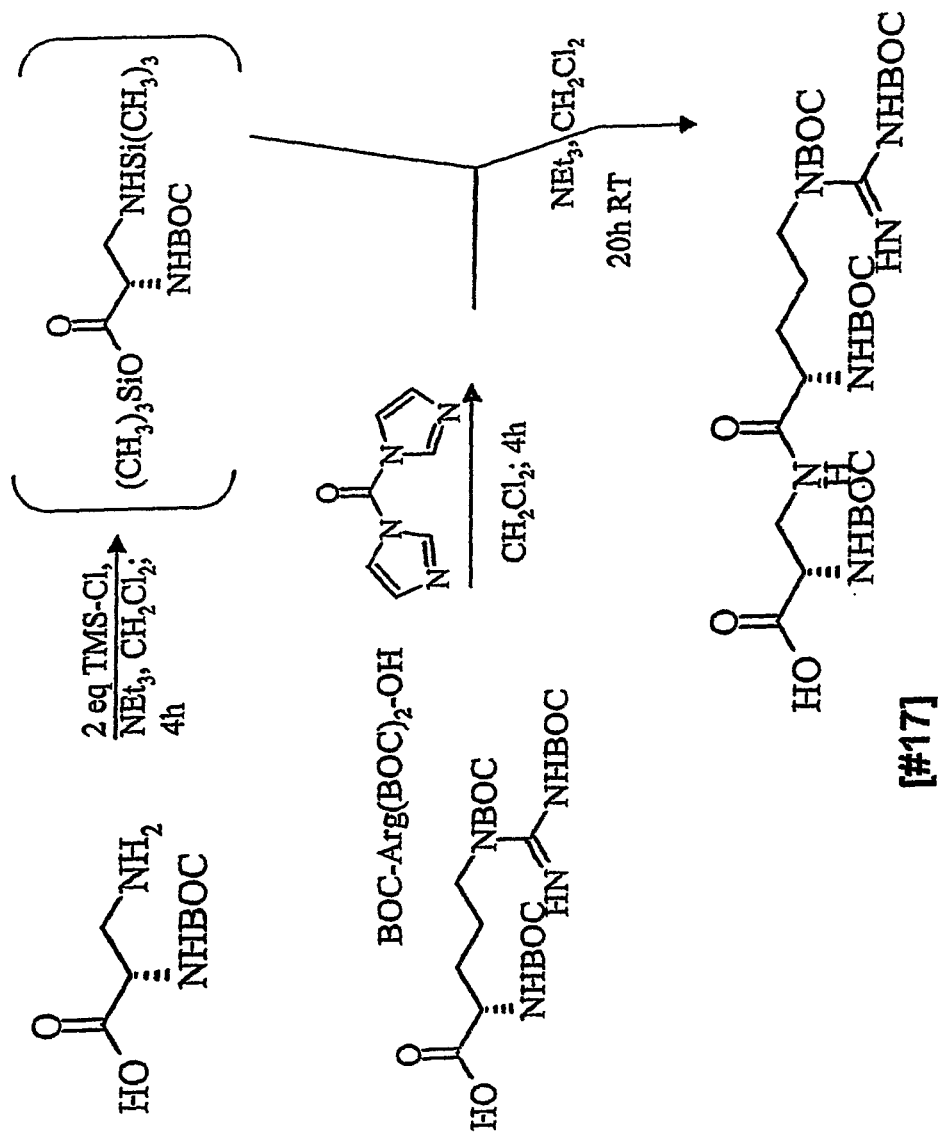
Fig. 11- part 1

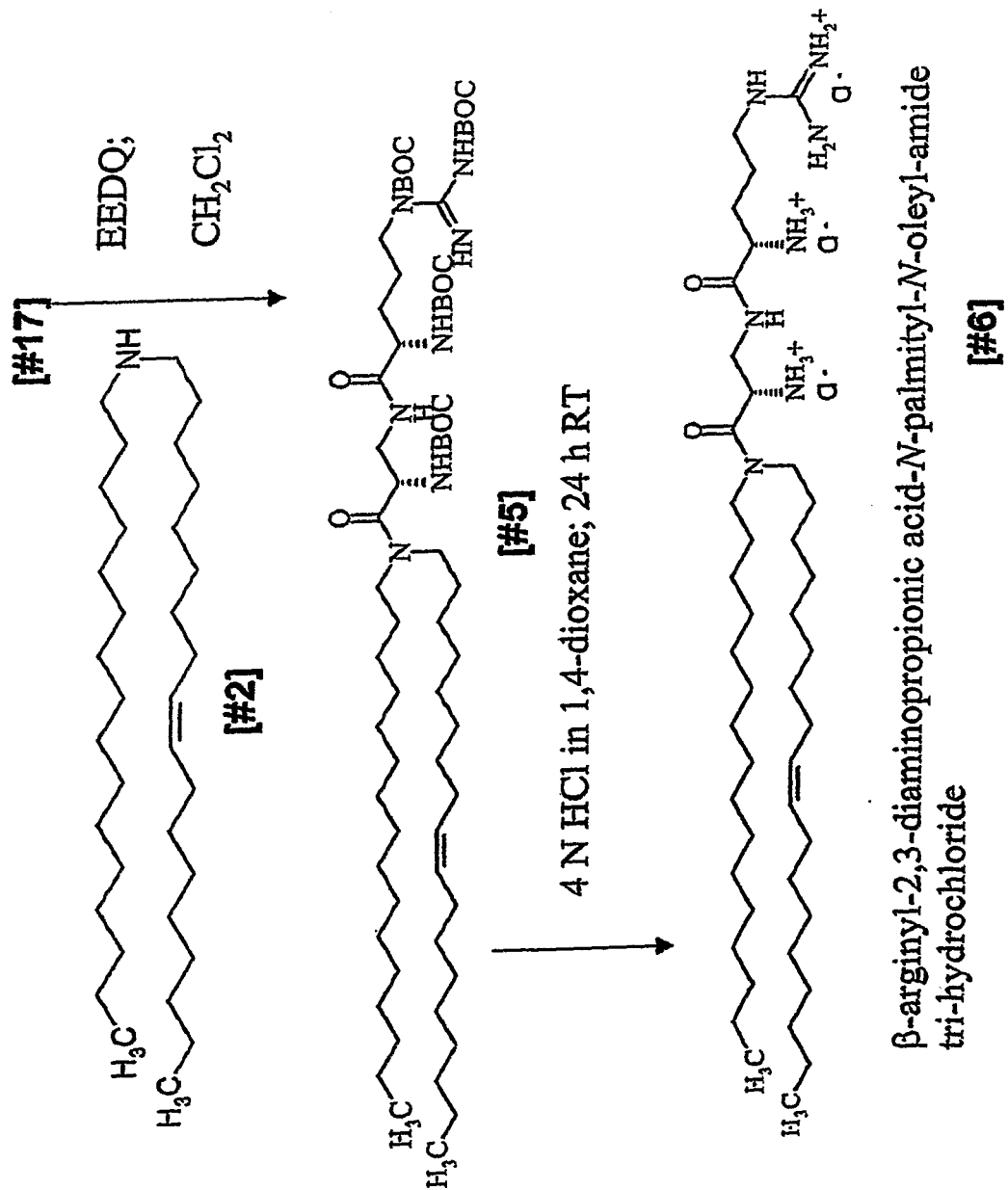
Fig. 11 – part 2

SEQUENCE LISTING

```
<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligo
<220> FEATURE:
<221> NAME/KEY: modified_base
<222> LOCATION: (2)
<223> OTHER INFORMATION: 2'-O-methyl nucleotide
<220> FEATURE:
<221> NAME/KEY: modified_base
<222> LOCATION: (4)
<223> OTHER INFORMATION: 2'-O-methyl nucleotide
<220> FEATURE:
<221> NAME/KEY: modified_base
<222> LOCATION: (6)
<223> OTHER INFORMATION: 2'-O-methyl nucleotide
<220> FEATURE:
<221> NAME/KEY: modified_base
<222> LOCATION: (8)
<223> OTHER INFORMATION: 2'-O-methyl nucleotide
<220> FEATURE:
<221> NAME/KEY: modified_base
<222> LOCATION: (10)
<223> OTHER INFORMATION: 2'-O-methyl nucleotide
<220> FEATURE:
<221> NAME/KEY: modified_base
<222> LOCATION: (12)
<223> OTHER INFORMATION: 2'-O-methyl nucleotide
<220> FEATURE:
<221> NAME/KEY: modified_base
<222> LOCATION: (14)
<223> OTHER INFORMATION: 2'-O-methyl nucleotide
<220> FEATURE:
<221> NAME/KEY: modified_base
<222> LOCATION: (16)
<223> OTHER INFORMATION: 2'-O-methyl nucleotide
<220> FEATURE:
<221> NAME/KEY: modified_base
<222> LOCATION: (18)
<223> OTHER INFORMATION: 2'-O-methyl nucleotide
<220> FEATURE:
<223> OTHER INFORMATION: 3' phosphate

<400> SEQUENCE: 1
uaaguucuag cuguggugg                                                  19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligo
<220> FEATURE:
<221> NAME/KEY: modified_base
<222> LOCATION: (2)
<223> OTHER INFORMATION: 2'-O-methyl nucleotide
<220> FEATURE:
<221> NAME/KEY: modified_base
```

```
<222> LOCATION: (4)
<223> OTHER INFORMATION: 2'-O-methyl nucleotide
<220> FEATURE:
<221> NAME/KEY: modified_base
<222> LOCATION: (6)
<223> OTHER INFORMATION: 2'-O-methyl nucleotide
<220> FEATURE:
<221> NAME/KEY: modified_base
<222> LOCATION: (8)
<223> OTHER INFORMATION: 2'-O-methyl nucleotide
<220> FEATURE:
<221> NAME/KEY: modified_base
<222> LOCATION: (10)
<223> OTHER INFORMATION: 2'-O-methyl nucleotide
<220> FEATURE:
<221> NAME/KEY: modified_base
<222> LOCATION: (12)
<223> OTHER INFORMATION: 2'-O-methyl nucleotide
<220> FEATURE:
<221> NAME/KEY: modified_base
<222> LOCATION: (14)
<223> OTHER INFORMATION: 2'-O-methyl nucleotide
<220> FEATURE:
<221> NAME/KEY: modified_base
<222> LOCATION: (16)
<223> OTHER INFORMATION: 2'-O-methyl nucleotide
<220> FEATURE:
<221> NAME/KEY: modified_base
<222> LOCATION: (18)
<223> OTHER INFORMATION: 2'-O-methyl nucleotide
<220> FEATURE:
<223> OTHER INFORMATION: 3' phosphate

<400> SEQUENCE: 2
ccaccacagc uagaacuua                                                19
```

COATED LIPID COMPLEXES AND THEIR USE

This application is a National Stage entry under 35 U.S.C. 371 of PCT/EP2005/014074, filed Dec. 27, 2005, which claims priority to EP 04030846.2 filed Dec. 27, 2004, both of which are hereby incorporated by reference in their entireties.

The present invention is related to cationic lipids, compositions containing the same and use thereof as well as a method for transferring chemical compounds into cells.

Both molecular biology as well as molecular medicine heavily rely on the introduction of biologically active compounds into cells. Such biologically active compounds typically comprise, among others, DNA, RNA as well as peptides and proteins, respectively. The barrier which has to be overcome is typically a lipid bilayer which has a negatively charged outer surface. In the art, a number of technologies have been developed to penetrate the cellular membrane and to thus introduce the biologically active compounds. Some methods conceived for laboratory use, however, cannot be used in the medical field and are more particularly not suitable for drug delivery. For example, electroporation and ballistic methods known in the art, would, if at all, only allow a local delivery of biologically active compounds. Apart from said lipid bilayer cellular membranes also comprise transporter systems. Accordingly, efforts were undertaken to use these kinds of transporter systems in order to transfer the biologically active compounds across the cell membrane. However, due to the specificity or cross-reactivity of such transporter systems, their use is not a generally applicable method.

A more generally applicable approach described in the art for transferring biologically active compounds into cells, is the use of viral vectors. However, viral vectors can be used only for transferring genes efficiently into some cell types; but they cannot be used to introduce chemically synthesised molecules into the cells.

An alternative approach was the use of so called liposomes (Bangham, J. Mol. Biol. 13, 238-252). Liposomes are vesicles which are generated upon association of amphiphilic lipids in water. Liposomes typically comprise concentrically arranged bilayers of phospholipids. Depending on the number of layers liposomes can be categorised as small unilamelar vesicles, multilamelar vesicles and large multilamelar vesicles. Liposomes have proven to be effective delivery agents as they allow to incorporate hydrophilic compounds into the aqueous intermediate layers, whereas hydrophobic compounds are incorporated into the lipid layers. It is well known in the art that both the composition of the lipid formulation as well as its method of preparation have an effect on the structure and size of the resultant lipid aggregates and thus on the liposomes. Liposomes are also known to incorporate cationic lipids.

Cationic lipids have, apart from being components of liposomes, also attracted considerable attention as they may as such be used for cellular delivery of biopolymers. Using cationic lipids any anionic compound can be encapsulated essentially in a quantitive manner due to electrostatic interaction. In addition, it is believed that the cationic lipids interact with the negatively charged cell membranes initiating cellular membrane transport. It has been found that the use of a liposomal formulation containing cationic lipids or the use of cationic lipids as such together with a biologically active compound requires a heuristic approach as each formulation is of limited use because it typically can deliver plasmids into some but not all cell types, usually in the absence of serum.

Charge and/or mass ratios of lipids and the biologically active compounds to be transported by them have turned out to be a crucial factor in the delivery of different types of said biologically active compounds. For example, it has been shown that lipid formulations suitable for plasmid delivery comprising 5,000 to 10,000 bases in size, are generally not effective for the delivery of oligonucleotides such as synthetic ribozymes or antisense molecules typically comprising about 10 to about 50 bases. In addition, it has recently been indicated that optimal delivery conditions for antisense oligonucleotides and ribozymes are different, even in the same cell type.

U.S. Pat. No. 6,395,713 discloses cationic lipid based compositions which typically consist of a lipophilic group, a linker and a head group and the use of such compositions for transferring biologically active compounds into a cell.

The problem underlying the present invention was to provide a means for introducing biologically active compounds into cells, preferably animal cells. A further problem underlying the present invention is to provide a delivery agent for nucleic acids, particularly small nucleic acids such as siRNA, siNA and RNAi or aptamers and spiegelmers.

A still further problem underlying the present invention is to provide a delivery agent which has good transfection and delivery characteristics while providing for a longer circulation time in vivo.

These problems are solved by the subject matter of the independent claims attached hereto. Preferred embodiments may be taken from the attached claims dependent thereon.

The problem underlying the present invention is also solved in a first aspect by a lipid composition comprising
  at least a first lipid component,
  at least a first helper lipid, and
  a shielding compound which is removable from the lipid composition under in vivo conditions.

In an embodiment of the first aspect the shielding compound is selected from the group comprising PEG, HEG, polyhydroxyethyl starch (polyHES) and a polypropylene.

In a preferred embodiment of the first aspect the shielding compound is PEG2000 or PEG5000.

In an embodiment of the first aspect the composition comprises a further constituent and/or a second helper lipid.

In an embodiment of the first aspect the lipid composition comprises a nucleic acid, whereby such nucleic acid is preferably the further constituent.

In a preferred embodiment of the first aspect the nucleic acid is selected from the group comprising RNAi, siRNA, siNA, antisense nucleic acid, ribozymes, aptamers and spiegelmers.

In an embodiment of the first aspect the shielding compound is a conjugate of PEG and ceramide.

In a preferred embodiment of the first aspect the ceramide comprises at least one short carbon chain substituent of from 6 to 10 carbon atoms, preferably of 8 carbon atoms.

In an embodiment of the first aspect the ceramide is the first helper lipid.

In an alternative embodiment of the first aspect the ceramide is the second helper lipid.

In an embodiment of the first aspect the shielding compound is attached to the nucleic acid.

In a preferred embodiment of the first aspect the shielding compound is attached to the nucleic acid by a linker moiety preferably covalently attached to the nucleic acid by a linker moiety.

In a more preferred embodiment of the first aspect the linker moiety is selected from the group comprising ssRNA, ssDNA, dsRNA, dsDNA, peptide, S—S-linkers and pH sensitive linkers.

In a preferred embodiment of the first aspect the nucleic acid is selected from the group comprising RNAi, siRNA and siNA and the linker is attached to the 3' end of the sense strand.

In a preferred embodiment of the first aspect the shielding compound comprises a pH-sensitive linker or a pH-sensitive moiety.

In a preferred embodiment of the first aspect the linker or moiety is an anionic linker or an anionic moiety In a more preferred embodiment of the first aspect the anionic linker or anionic moiety is less anionic or neutral in an acidic environment, whereby preferably such acidic environment is an endosome.

In an embodiment of the first aspect the pH-sensitive linker or the pH-sensitive moiety is selected from the group comprising oligo (glutamic acid), oligophenolate(s) and diethylene triamine penta acetic acid.

In an embodiment of the first aspect the first lipid component is a compound according to formula (I),

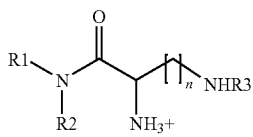

(I)

wherein $R_1$ and $R_2$ are each and independently selected from the group comprising alkyl;
n is any integer between 1 and 4;
$R_3$ is an acyl selected from the group comprising lysyl, ornithyl, 2,4-diaminobutyryl, histidyl and an acyl moiety according to formula (II),

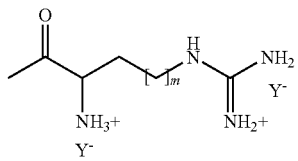

(II)

wherein m is any integer from 1 to 3, wherein the $NH_3^+$ is optionally absent, and $Y^-$ is a pharmaceutically acceptable anion.

In a preferred embodiment of the first aspect $R_1$ and $R_2$ are each and independently selected from the group comprising lauryl, myristyl, palmityl and oleyl.

In a more preferred embodiment of the first aspect $R_1$ is lauryl and $R_2$ is myristyl; or $R_1$ is palmityl and $R_2$ is oleyl.

In a more preferred embodiment of the first aspect m is 1 or 2.

In a more preferred embodiment of the first aspect the compound is a cationic lipid, preferably in association with an anion $Y^-$.

In a more preferred embodiment of the first aspect $Y^-$ is selected from the group comprising halogenids, acetate and trifluoroacetate.

In a more preferred embodiment of the first aspect the compound is selected from the group comprising β-arginyl-2,3-diamino propionic acid-N-palmityl-N-oleyl-amide trihydro chloride

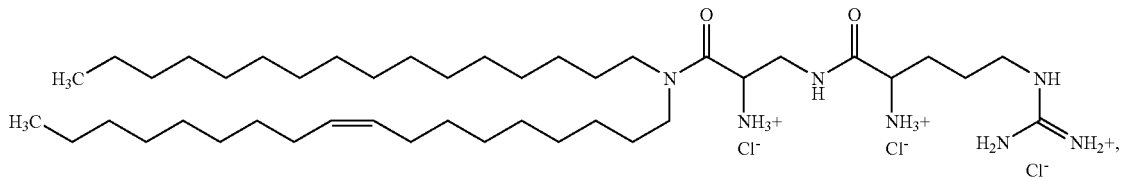

β-arginyl-2,3-diamino propionic acid-N-lauryl-N-myristyl-amide trihydrochloride

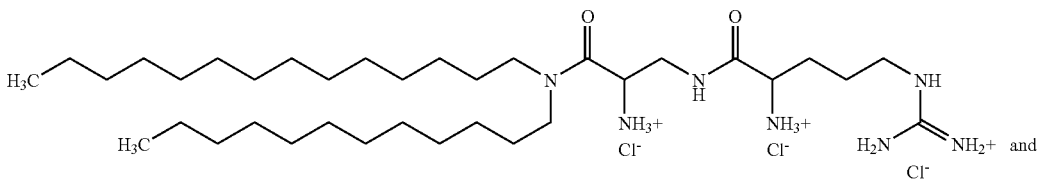 [SMILES: CCCCCCCCCCCCCCN(CCCCCCCCCCCC)C(=O)C([NH3+])CNC(=O)C([NH3+])CCCNC(N)=[NH2+] ; "and" ; [Cl-] ; [Cl-] ; [Cl-]]

and

ε-arginyl-lysine-N-lauryl-N-myristyl-amide trihydrochloride

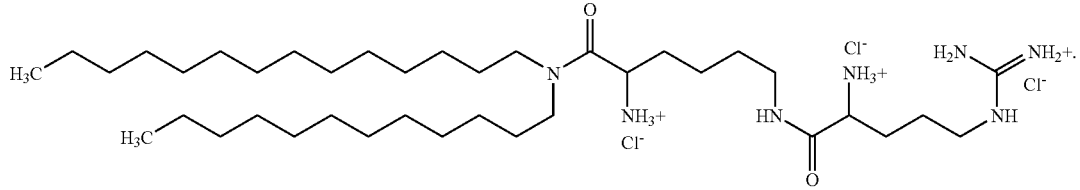

In a more preferred embodiment of the first aspect the composition comprises a carrier.

The problem underlying the present invention is also solved in a second aspect by a pharmaceutical composition comprising a composition according to the first aspect and a pharmaceutically active compound and preferably a pharmaceutically acceptable carrier.

In an embodiment of the second aspect the pharmaceutically active compound and/or the further constituent is selected from the group comprising peptides, proteins, oligonucleotides, polynucleotides and nucleic acids.

In a preferred embodiment of the second aspect the protein is an antibody, preferably a monoclonal antibody.

In an alternative preferred embodiment the nucleic acid is selected from the group comprising DNA, RNA, PNA and LNA.

In a preferred embodiment of the second aspect the nucleic acid is a functional nucleic acid, whereby preferably the functional nucleic acid is selected from the group comprising RNAi, siRNA, siNA, antisense nucleic acid, ribozymes, aptamers and spiegelmers.

In a embodiment of the first and the second aspect the first helper lipid and/or the second helper lipid is selected from the group comprising phospholipids and steroids, preferably under the proviso that the first and/or the second helper lipid is different from a ceramide.

In a preferred embodiment of the first and the second aspect the first and/or second helper lipid or helper lipid component is selected from the group comprising 1,2-diphytanoyl-sn-glycero-3-phosphoethanolamine and 1,2-dioleyl-sn-glycero-3-phosphoethanolamine.

In a more preferred embodiment of the first and the second aspect the content of the helper lipid component is from about 20 mol % to about 80 mol % of the overall lipid content of the composition.

In an even more preferred embodiment of the first and the second aspect the content of the helper lipid component is from about 35 mol % to about 65 mol %.

In an embodiment of the first and the second aspect the lipid is β-arginyl-2,3-diamino propionic acid-N-palmityl-N-oleyl-amidtrihydrochloride, and the helper lipid is 1,2-diphytanoyl-sn-glycero-3-phosphoethanolamine.

In a preferred embodiment of the first and the second aspect the lipid is 50 mol % and the helper lipid is 50 mol % of the overall lipid content of the composition.

In an embodiment of the first and the second aspect the composition further comprises a second helper lipid.

In an embodiment of the first and the second aspect the first and/or the second helper lipid comprises a group which is selected from the group comprising a PEG moiety, a BEG moiety, a polyhydroxyethyl starch (polyHES) moiety and a polypropylene moiety, whereby such moiety preferably provides a molecule weight from about 500 to 10000 Da, more preferably from about 2000 to 5000 Da.

In a preferred embodiment of the first and the second aspect the helper lipid comprising the PEG moiety is selected from the group comprising 1,2-distearoyl-sn-glycero-3-phosphoethanolamine and 1,2-dialkyl-sn-glycero-3-phosphoethanolamine.

In a more preferred embodiment of the first and the second aspect the PEG moiety of the helper lipid has a molecular weight from 2,000 to 5,000 Da, preferably a molecular weight of 2,000 Da.

In an even more preferred embodiment of the first and the second aspect the composition comprises as the lipid component β-arginyl-2,3-diamino propionic acid-N-palmityl-N-oleyl-amide trihydrochloride, as a first helper lipid 1,2-diphytanoyl-sn-glycero-3-phosphoethanolamine and as a second helper lipid 1,2-distearoyl-sn-glycero-3-phosphoethanolamine-PEG2000.

In an embodiment of the first and the second aspect the content of the second helper lipid is from about 0.05 mol % to 4.9 mol %, preferably about 1 to 2 mol %.

In an embodiment of the first and the second aspect the composition contains from about 1 to 10 mol %, more preferably 1 to 7.5 mol % and most preferably 1 to 5 mol % of the conjugate of PEG and the ceramide.

In a preferred embodiment of the first and the second aspect the ceramid is C8m and PEG is PEG 2000 and wherein the content of the conjugate of PEG and the ceramide is from about 1 to 7.5 mol %.

In an alternative preferred embodiment of the first and the second aspect the ceramide is C8m and PEG is PEG5000 and wherein the content of the conjugate of PEG and ceramide is from about 1 to 5 mol %.

In an embodiment of the first and the second aspect the content of the first lipid component is from about 42.5 mol % to 50 mol %, the content of the first helper lipid is from about 42.5 to 50 mol %, whereby the sum of the content of the first lipid component, of the first helper lipid and of the conjugate of PEG and ceramide is 100 mol %.

In an embodiment of the first and the second aspect the functional nucleic acid is a double-stranded ribonucleic acid, wherein the composition further comprises a nucleic acid, preferably a functional nucleic acid which is more preferably a double-stranded ribonucleic acid and most preferably a nucleic acid selected from the group comprising RNAi, siRNA, siNA, antisense nucleic acid and ribozyme, whereby preferably the molar ration of RNAi to cationic lipid is from about 0 to 0.075, preferably from about 0.02 to 0.05 and even more preferably 0.037.

In an embodiment of the first and the second aspect the first lipid component and/or at least one of the helper lipids and/or the shielding compound is/are present as a dispersion in an aqueous medium.

In an alternative embodiment of the first and the second aspect the first lipid component and/or at least one of the helper lipids and/or the shielding compound is/are present as a solution in a water miscible solvent, whereby preferably the solvent is selected from the group comprising ethanol and tert.-butanol.

The problem underlying the present invention is also solved in a third aspect by the use of a composition according to the first or the second aspect for the manufacture of a medicament.

The problem underlying the present invention is also solved in a fourth aspect by the use of a composition according to the first or the second aspect as a transferring agent.

In an embodiment of the fourth aspect the transferring agent transfer a pharmaceutically active component and/or a further constituent into a cell, preferably a mammalian cell and more preferably a human cell.

The problem underlying the present invention is also solved in a fifth aspect by a method for transferring a pharmaceutically active compound and/or a further constituent into a cell or across a membrane, preferably a cell membrane, comprising the following steps:

providing the cell or the membrane;
providing a composition according to the first or the second aspect the pharmaceutically active compound and/or the further constituent; and
contacting the cell or the membrane with the composition according to the first or the second aspect.

In an embodiment of the fifth aspect the method comprises as further step:

detecting the pharmaceutically active compound and/or the further constituent in the cell and/or beyond the membrane.

The present inventors have surprisingly found that a very effective delivery in in vivo applications of nucleic acids, in particular small nucleic acids such as RNAi, siRNA and siNA, can be achieved by using a lipid composition comprising at least a first lipid component, at least a first helper lipid and a shielding compound. The shielding compound provides for a longer circulation time in vivo and thus allows for a better biodistribution of the nucleic acid containing lipid composition. By this mechanism, it is possible to target sites within a human or animal body which are comparatively remote from the site of administration of such lipid composition as the lipid composition is not immediately absorbed by the tissue surrounding the injection site, usually the endothelial lining of the vasculature when an intravenous administration is performed. The shielding compound as used herein is preferably a compound which avoids the immediate interaction of the lipid composition with serum compounds or compounds of other bodily fluids or cytoplasma membranes, preferably cytoplasma membranes of the endothelial lining of the vasculature into which the lipid composition is preferably administered. The term shielding also means that elements of the immune system do not immediately interact with the lipid composition again increasing its circulation time in a living organism. Insofar, the shielding compound acts as an anti opsonizing compound. Without wishing to be bound by any mechanism or theory, it seems that the shielding compound forms a cover or coat which reduces the surface area of the lipid composition available for interaction with its environment which would otherwise result in the lipid composition fusing with other lipids or being bound by factors of the human and animal body, respectively, at a time which is too early for such interaction, although it has to be acknowledged that at a later stage, i.e. after a prolonged time upon administration of the lipid composition, such interaction is usually preferred at least to a certain extent so as to provide the delivery. Another mechanism on which the observed efficacy of the shielding compound seems to be based is the shielding of the overall charge of the lipid composition and in particular of the lipid composition containing a nucleic acid, preferably a functional nucleic acid as defined herein and more preferably a siRNA, siNA and RNAi. Again, the interaction of the lipid composition seems to be affected, whereby the effect arises from the shielding of the charges rather than the shielding of the lipid components. In connection with the present disclosure, it is to be acknowledged that a composition can comprise as little as one lipid.

The shielding compound is preferably a biologically inert compound. More preferably, the shielding compound does not carry any charge on its surface or on the molecule as such. Particularly preferred shielding compounds are thus polyethylenglycoles, hydroxyethylglucose based polymers, polyhydroxyethyl starch (polyHES) and polypropylene, whereby any of said compounds preferably has a molecule weight from about 500 to 10000 Da, more preferably from about 2000 to 5000 Da.

It is an important feature of the present invention that the shielding compound is removable from the lipid composition under in vivo conditions. Such removal exposes the other components of the lipid composition or part thereof to the environment such as the animal and human body, and ultimately allows the release and delivery, respectively, of a compound such as a nucleic acid contained in the lipid composition. The term in vivo conditions preferably means the conditions existing in an animal or human body, preferably in any bodily fluid such as blood, interstitium and intracellular liquids, and/or those existing in an endosome and/or lysosome. Depending on the design of the shielding compound, the removal can be affected in various ways as will be described in more detail in the following.

A further effect arising from the loss of the shielding agent, particularly if the shielding agent is PEG, is due to the fact that providing lipid formulations with PEG which is also referred to as PEGylation, often results in an impaired functional delivery of the nucleic acid molecules to be delivered by such lipid formulation into the cytoplasm. The bulky presence of the PEG at the lipid formulation impairs the endosomal uptake of the liposomes typically formed by the lipid formulation or interferes with the necessary endosomale escape of the nucleic acid contained or associated with the lipid composition.

In one embodiment, the shielding compound is selected from the group comprising PEG, HEG, polyhydroxyethyl starch (polyHES) and polypropylene, which is attached, preferably covalently attached, to a ceramide. The ceramide interacts with the lipid compound and, if present, with a helper lipid. Insofar, the ceramide can be either the first helper lipid or a second helper lipid. It is preferred that the ceramide conjugated to PEG is different from the first helper lipid. The ceramide is embedded into the lipid fraction of the lipid composition preferably formed by the first lipid component and the first helper lipid and will be released due to the comparatively short hydrocarbon chain at a certain rate. When the ceramide is thus released from the lipid composition, so is the shielding agent. Therefore, in this embodiment, the in vitro conditions allow for the desintegration of the lipid formulation and thus provides a prolonged lifetime or circulation time in vivo of the lipid composition.

In a further embodiment, the shielding agent is attached to a nucleic acid contained in the lipid composition or associated therewith. Preferably, the shielding agent is covalently linked to the nucleic acid, most preferably through a linker. In a more preferred embodiment, the linker is designed such that it is cleaved under physiological conditions, i.e. conditions prevailing in an animal or human organism. In a preferred embodiment only a certain percentage of the nucleic acid is actually provided with such polymer through a linker. Without wishing to be bound by any theory, it seems that it is sufficient that only a certain number of nucleic acid molecules forming part of the lipid composition has to have such a bulky moiety so as to provide the shielding effect to said lipid composition. Preferably, the portion of nucleic acid molecules ranges from about 0 to 20%, more preferably 3 to 10%, and even more preferably from 6 to 10%. Preferred contents of nucleic acids having the shielding agent (which is also referred to herein as the shielding compound) are from about 0 to 3%, 3 to 6%, 6 to 10% and 10 to 20%, whereby % as used in this paragraph and throughout the present application, if not indicated to the contrary, is mole %.

Such linker can be a single-stranded RNA linker, more preferably comprising 1 to 20 nucleotides which will be cleaved by RNA endonuclease activity existing in or under in vivo conditions. In a further embodiment, the linker is formed by a single-stranded DNA linker which is cleaved by DNA endonucleases also present in or under in vivo conditions. In further embodiments, the linker can be formed by a double-stranded RNA or a double-stranded DNA. The stability of the linker consisting of a nucleic acid is typically as follows: ssRNA<dsRNA,<ssDNA<<dsDNA. Such stability variety allows for a specific design of the residual time of the nucleic acid thus modified and the lipid composition, respectively, comprising such linker.

In a further embodiment, the linker can be formed by a oligopeptide, polypeptide or protein which is cleaved by proteases present in or under in vivo conditions. A still further embodiment provides a linker comprising an S—S-linkage which is sensitive to redox conditions.

In an even still further embodiment the linker is a pH sensitive linker. The concept of a pH sensitive linker resides in the observation that upon internalisation of a lipid composition which can, in principle, be either a lipoplex or a liposome, any shielding agent which is clearly advantageous when it comes to the protection of the lipid composition prior to internalisation can impose a limitation of the further use of the compounds thus transferred into the cell. As used herein, the shielding agent is coupled to the pH sensitive linker which is or comprises in a preferred embodiment an anionic moiety. In an acidic environment such as an endosome, the charge of such anionic moiety is changed. Because of this, the interaction of the pH sensitive linker with the cationic lipid contained in the lipid formulation based on electrostatics is also changed, usually reduced which results in a more or less gradual release of the pH sensitive linker from the cationic lipid comprising lipid formulation. Consequently, the liposome becomes devoid of the shielding agent and can thus exert its impact in the cell. This kind of linker comprises both linkers which are as such known in the art and new linkers of this kind, i.e. having this kind of characteristics. Preferably, such linker is any linker which has a charge characteristic which allows the linker to react as described above. Representatives of such pH sensitive linkers comprise, but are not limited to, oligo(glutamic acid), oligophenolates, and diethylene triamine penta acetic acid. Both the coupling of such linker to the shielding agent and the incorporation of such linker into the shielding agent which is then commonly referred to as a moiety of the shielding agent is known to the ones skilled in the art.

The compound used as the first lipid component in the lipid composition according to the present invention which is also referred to herein as the compound(s) according to the present invention can, as depicted in FIG. 1, can be regarded as to comprise a lipophilic group formed by the R1-N—R2 moiety, a linker group formed by the C(O)—CH(NH$_3^+$) (CH$_2$)$_n$—NH moiety and a head group formed by the R3 moiety. The present inventor has surprisingly found that this kind of compound exhibiting a positive charge at the linker group is particularly suitable to transfer biologically active compounds over a cell membrane and preferably into cells, more preferably animal cells. Also, the present inventor has surprisingly found that the transfer mediated by the compounds according to the present invention will be particularly effective if the biologically active compound is a nucleic acid, more preferably siRNA and siNA.

As preferably used herein, the term alkyl refers to a saturated aliphatic radical containing from 8 to 20 carbon atoms, preferably 12 to 18 carbon atoms, or a mono- or polyunsaturated aliphatic hydrocarbon radical containing from 8 to 30 carbon atoms, containing at least one double and triple bond, respectively. Thus, in a preferred embodiment, the term alkyl also comprises alkenyl and alkinyl. Alky refers to both branched and unbranched, i.e. non-linear or straight chain alkyl groups. Preferred straight chain alkyl groups contain from 8 to 30 carbon atoms. More preferred straight chain alkyl groups contain from 12 to 18 carbon atoms. Preferred branched alkyl groups contain from 8 to 30 carbon atoms, whereby the number from 8 to 30 carbon atoms refers to the number of carbon atoms forming the backbone of such branched alkyl group. The backbone of the branched alkyl group contains at least one alkyl group, as branching off from the backbone, with the alkyl group being defined as herein, more preferably with the alkyl group comprising short chain alkyl groups, more preferably comprising from 1 to 6, even more preferred 1 to 3 and most preferred 1 C atom. More preferred are branched alkyl groups containing 12 to 18 carbon atoms in the backbone with the branching alkyl groups being defined as in the foregoing. A particularly preferred alkyl group is the phytanyl group.

In an alternative embodiment, the alkyl is an unsaturated branched or unbranched alkyl group as defined above. More preferably, such unsaturated aliphatic hydrocarbon radical contains 1, 2 or 3 or 4 double bonds, whereby a radical having one double bond is particularly preferred. Most preferred is oleyl which is C18: 1delta9, i.e. an aliphatic hydrocarbon radical having 18 C atoms, whereby at position 9 a cis configured double bond is presented rather than a single bond linking C atom number 9 to C atom number 10.

As used herein, n is any integer between 1 and 4, which means that n may be 1, 2, 3 and 4. As used herein, m is any integer between 1 and 3, which means that m may be 1, 2 and 3.

It is to be understood that the compounds according to the present invention are preferably cationic lipids. More preferably, any of the NH or NH$_2$ groups present in the compounds according to the present invention are present in a protonated form. Typically, any positive charge of the compound according to the present invention is compensated by the presence of an anion. Such anion can be a monovalent or polyvalent anion. Preferred anions are halides, acetate and trifluoroacetate. Halides as used herein are preferably fluorides, chlorides, iodides and bromides. Most preferred are chlorides. Upon association of the cationic lipid and the biologically active compound to be transferred into a cell, the halide anion is replaced by the biologically active compound which preferably exhibits one or several negative charges, although it has to be acknowledged that the overall charge of the biologically active compound is not necessarily negative.

It is to be acknowledged that any compound according to formula (I) comprises at least two asymmetric C atoms. It is within the present invention that any possible enantiomer of such compound is disclosed herein, i.e. in particular the R—R; S—S; R—S and S—R enantiomer.

The compounds according to the present invention can form a composition or be part of a composition, whereby such composition comprises a carrier. In such composition which is also referred to herein as lipid composition the compounds according to the present invention are also referred to as the lipid component(s). Such carrier is preferably a liquid carrier. Preferred liquid carriers are aqueous carriers and non-aqueous carriers. Preferred aqueous carriers are water, aqueous buffer systems, more preferably buffer systems having a physiological buffer strength and physiological salt concentration(s). Preferred non-aqueous carriers are solvents, preferably organic solvents such as ethanol, and tert.-butanol. Without wishing to be bound by any theory, any water miscible organic solvent can, in principle, be used. It is to be acknowledged that the composition, more particularly the lipid composition can thus be present as or form liposomes.

The composition according to the present invention may comprise one or more helper lipids which are also referred to herein as helper lipid components. The helper lipid components are preferably selected from the group comprising phospholipids and steroids. Phospholipids are preferably di- and monoester of the phosphoric acid. Preferred members of the phospholipids are phosphoglycerides and sphingolipids. Steroids, as used herein, are naturally occurring and synthetic compounds based on the partially hydrogenated cyclopenta [a]phenanthrene. Preferably, the steroids contain 21 to 30 C atoms. A particularly preferred steroid is cholesterol.

Particularly preferred helper lipids are 1,2-diphytanoyl-sn-glycero-3-phosphoethanolamine (DPhyPE) and 1,2-dioleoyl-sn-glycero-3-phosphoethanolamine (DOPE).

Particularly preferred compositions according to the present invention comprise any of β-arginyl-2,3-diaminopropionic acid-N-palmityl-N-oleyl-amide trihydrochloride [#6], β-arginyl-2,3-diaminopropionic acid-N-lauryl-N-myristyl-amide trihydrochloride [#11] or ε-arginyl-lysine-N-lauryl-N-myristyl-amide trihydrochloride [#15] in combination with DPhyPE, whereby the content of DPhyPE is from about 90 to 20 mol %, preferably 80 mol %, 65 mol %, 50 mol % and 35 mol %, whereby the term mol % refers to the percentage of the overall lipid content of the composition, i.e. the lipid content of the composition including the cationic lipid according to the present invention and any additional lipid, including, but not limited to, any helper lipid.

It is within the present invention that the composition according to the present invention preferably comprises the compound according to the present invention and/or one or several of the helper lipid(s) as disclosed herein, whereby either the compound according to the present invention, i.e. the cationic lipid, and/or the helper lipid component is present as a dispersion in an aqueous medium. Alternatively, the compound according to the present invention, i.e. the cationic lipid, and/or the helper lipid component is/are present as a solution in a water miscible solvent. As an aqueous medium, preferably any of the aqueous carrier as disclosed herein is used. Preferred water miscible solvents are any solvent which form a homogenous phase with water in any ratio. Preferred solvents are ethanol and tert.-butanol. It is to be acknowledged that the composition, more particularly the lipid composition can thus be present as or form liposomes.

It is to be acknowledged that the composition according to the present invention in its various embodiments is and may thus also be used as a pharmaceutical composition. In the latter case, the pharmaceutical composition comprises a pharmaceutically active compound and optionally a pharmaceutically acceptable carrier. Such pharmaceutically acceptable carrier may, preferably, be selected from the group of carriers as defined herein in connection with the composition according to the present invention. It will be understood by those skilled in the art that any composition as described herein may, in principle, be also used as a pharmaceutical composition provided that its ingredients and any combination thereof is pharmaceutically acceptable. A pharmaceutical composition comprises a pharmaceutically active compound. Such pharmaceutically active compound can be the same as the further constituent of the composition according to the present invention which is preferably any biologically active compound, more preferably any biologically active compound as disclosed herein. The further constituent, pharmaceutically active compound and/or biologically active compound are preferably selected from the group comprising peptides, proteins, oligonucleotides, polynucleotides and nucleic acids.

Preferably, any such biologically active compound is a negatively charged molecule. The term negatively charged molecule means to include molecules that have at least one negatively charged group that can ion-pair with the positively charged group of the cationic lipid according to the present invention, although the present inventor does not wish to be bound by any theory. In principle, the positive charge at the linker moiety could also have some effect on the overall structure of either the lipid as such or any complex formed between the cationic lipid and the negatively charged molecule, i.e. the biologically active compound. Apart from that, the additional positive charge introduced into the lipid according to the present invention compared to the cationic lipids disclosed in U.S. Pat. No. 6,395,713, should contribute to an increased toxicity of this lipid as taught by Xu Y, Szoka F C Jr.; Biochemistry; 1996 May 7, 35 (18): 5616-23. In contrast to what the one skilled in the art would have expected from this document of the prior art the compounds according to the present invention are particularly suitable for the various purposes disclosed herein and are in particular devoid of any increased toxicity.

A peptide as preferably used herein is any polymer consisting of at least two amino acids which are covalently linked to each other, preferably through a peptide bond. More preferably, a peptide consists of two to ten amino acids. A particularly preferred embodiment of the peptide is an oligopeptide which even more preferably comprises from about 10 to about 100 amino acids. Proteins as preferably used herein are polymers consisting of a plurality of amino acids which are covalently linked to each other. Preferably such proteins comprise about at least 100 amino acids or amino acid residues.

A preferred protein which may be used in connection with the cationic lipid and the composition according to the present invention, is any antibody, preferably any monoclonal antibody.

Particularly preferred biologically active compounds, i.e. pharmaceutically active compounds and such further constituent as used in connection with the composition according to the present invention are nucleic acids. Such nucleic acids can be either DNA, RNA, PNA or any mixture thereof. More preferably, the nucleic acid is a functional nucleic acid. A functional nucleic acid as preferably used herein is a nucleic acid which is not a nucleic acid coding for a peptide and protein, respectively. Preferred functional nucleic acids are siRNA, siNA, RNAi, antisense-nucleic acids, ribozymes, aptamers and spiegelmers which are all known in the art.

siRNA are small interfering RNA as, for example, described in international patent application PCT/EP03/08666. These molecules typically consist of a double-stranded RNA structure which comprises between 15 to 25, preferably 18 to 23 nucleotide pairs which are base-pairing to each other, i.e. are essentially complementary to each other, typically mediated by Watson-Crick base-pairing. One strand of this double-stranded RNA molecule is essentially complementary to a target nucleic acid, preferably a mRNA, whereas the second strand of said double-stranded RNA molecule is essentially identical to a stretch of said target nucleic acid. The siRNA molecule may be flanked on each side and each stretch, respectively, by a number of additional oligonucleotides which, however, do not necessarily have to base-pair to each other.

RNAi has essentially the same design as siRNA, however, the molecules are significantly longer compared to siRNA. RNAi molecules typically comprise 50 or more nucleotides and base pairs, respectively.

A further class of functional nucleic acids which are active based on the same mode of action as siRNA and RNAi is siNA. siNA is, e.g., described in international patent application PCT/EP03/074654. More particularly, siNA corresponds to siRNA, whereby the siNA molecule does not comprise any ribonucleotides.

Antisense nucleic acids, as preferably used herein, are oligonucleotides which hybridise based on base complementarity with a target RNA, preferably mRNA, thereby activating RNaseH. RNaseH is activated by both phosphodiester and phosphothioate-coupled DNA. Phosphodiester-coupled DNA, however, is rapidly degraded by cellular nucleases with exception of phosphothioate-coupled DNA. Antisense polynucleotides are thus effective only as DNA-RNA hybrid complexes. Preferred lengths of antisense nucleic acids range from 16 to 23 nucleotides. Examples for this kind of antisense oligonucleotides are described, among others, in U.S. Pat. No. 5,849,902 and U.S. Pat. No. 5,989,912.

A further group of functional nucleic acids are ribozymes which are catalytically active nucleic acids preferably consisting of RNA which basically comprise two moieties. The first moiety shows a catalytic activity, whereas the second moiety is responsible for a specific interaction with the target nucleic acid. Upon interaction between the target nucleic acid and the said moiety of the ribozyme, typically by hybridisation and Watson-Crick base-pairing of essentially complementary stretches of bases on the two hybridising strands, the catalytically active moiety may become active which means that it cleaves, either intramolecularly or intermolecularly, the target nucleic acid in case the catalytic activity of the ribozyme is a phosphodiesterase activity. Ribozymes, the use and design principles thereof are known to the ones skilled in the art and, for example, described in Doherty and Doudna (Annu. Ref. Biophys. Biomolstruct. 2000; 30: 457-75).

A still further group of functional nucleic acids are aptamers. Aptamers are D-nucleic acids which are either single-stranded or double-stranded and which specifically interact with a target molecule. The manufacture or selection of aptamers is, e.g., described in European patent EP 0 533 838. In contrast to RNAi, siRNA, siNA, antisense-nucleotides and ribozymes, aptamers do not degrade any target mRNA but interact specifically with the secondary and tertiary structure of a target compound such as a protein. Upon interaction with the target, the target typically shows a change in its biological activity. The length of aptamers typically ranges from as little as 15 to as much as 80 nucleotides, and preferably ranges from about 20 to about 50 nucleotides.

Another group of functional nucleic acids are spiegelmers as, for example, described in international patent application WO 98/08856. Spiegelmers are molecules similar to aptamers. However, spiegelmers consist either completely or mostly of L-nucleotides rather than D-nucleotides in contrast to aptamers. Otherwise, particularly with regard to possible lengths of spiegelmers, the same applies to spiegelmers as outlined in connection with aptamers.

As mentioned previously, the present inventor has surprisingly found that the compound according to the present invention and the respective compositions comprising such compound can be particularly effective in transferring RNAi, and more particularly siRNA and siNA into a cell. It is to be noted that although not wishing to be bound by any theory, due to the particular mol percentages of the helper lipid(s) contained in the lipid compositions according to the present invention, which helper lipid can be either a PEG-free helper lipid or in particular a PEG-containing helper lipid, surprising effects can be realised, more particularly if the content of any of this kind of helper lipid is contained within the concentration range specified herein. In connection therewith, it is particularly noteworthy that if the composition according to the present invention contains a helper lipid comprising a PEG moiety, any delivery or transfection action using such PEG-derived helper lipid containing composition is particularly effective in delivering nucleic acid, particularly RNAi molecules, most particularly siRNA, siNA, antisense nucleotides and ribozymes.

The reason for this is that the present inventors have surprisingly found that liposomes containing more than about 4% of PEG-containing helper lipid(s) are not active, whereas liposomes with, less than 4% (preferably less than 3% but more than 0%) do mediate functional delivery. Basically, the present inventors have discovered that the specific amount of PEG in the lipid compositions according to the present invention is suitable to provide for an effective transfection and delivery, respectively.

In a further aspect the present inventors have surprisingly found that the lipid compositions according to the present invention which are preferably present as lipoplexes or liposomes, preferably show an overall cationic charge and thus an excess of at least one positive charge. More preferably, the lipid compositions exhibit a charge ratio negative:positive of from about 1:1.3 to 1:5. Therefore, the present invention is thus related in a further aspect to any lipid composition comprising at least one cationic lipid and a nucleic acid, preferably a RNAi, siRNA or siNA or any other of the functional nucleic acids defined herein, having a charge ratio negative: positive of from about 1:1.3 to 1:5. The cationic lipid is preferably any cationic lipid described herein. The lipid composition comprises in a preferred embodiment any helper lipid or helper lipid combination as described herein.

The present inventors have also found that in particular the molar ratio of siRNA and the cationic lipid can be crucial for the successful application of the lipid composition according to the present invention, especially in view of what has been said above in relation to the cationic overall charge of the nucleic acid containing lipid formulations. Without wishing to be bound by any theory it seems that 1 mole of cationic lipid, particularly as disclosed herein, can provide for a maximum of three positive charges per molecule, whereas the nucleic acid and more particularly the siRNA molecules as disclosed herein, provide for a maximum of 40 negative charges per molecule. In order to reach an overall positive charge of the siRNA containing lipid formulations according to the present invention, the molar ratio can range from 0 to a maximum of 0.075. A preferred molar ration range is from about 0.02 to 0.05 and even more preferred is a molar ratio range of about 0.037.

It is within the present invention that the composition and more particularly the pharmaceutical composition may comprise one or more of the aforementioned biologically active compounds which may be contained in a composition according to the present invention as pharmaceutically active compound and as further constituent, respectively. It will be acknowledged by the ones skilled in the art that any of these compounds can, in principle, be used as a pharmaceutically active compound. Such pharmaceutically active compound is typically directed against a target molecule which is involved in the pathomechanism of a disease. Due to the general design principle and mode of action underlying the various biologically active compounds and thus the pharmaceutically active compounds as used in connection with any aspect of the present invention, virtually any target can be addressed. Accordingly, the compound according to the present invention and the respective compositions containing the same can be used for the treatment or prevention of any disease or diseased condition which can be addressed, prevented and/or treated using this kind of biologically active compounds. It is to be acknowledged that apart from these biologically active compounds also any other biologically active compound can be part of a composition according to any embodiment of the present invention. Preferably such other biologically active compound comprises at least one negative charge, preferably under conditions where such other biologically active compound is interacting or complexed with the compound according to the present invention, more preferably the compound according to the present invention which is present as a cationic lipid.

As used herein, a biologically active compound is preferably any compound which is biologically active, preferably exhibits any biological, chemical and/or physical effects on a biological system. Such biological system is preferably any biochemical reaction, any cell, preferably any animal cell, more preferably any vertebrate cell and most preferably any mammalian cell, including, but not limited to, any human cell, any tissue, any organ and any organism. Any such organism is preferably selected from the group comprising mice, rats, guinea pigs, rabbits, cats, dogs, sheep, pigs, goats, cows, horses, poultry, monkeys and humans.

It is also within the present invention that any of the compositions according to the present invention, more particularly any pharmaceutical composition according to the present invention may comprise any further pharmaceutically active compound(s).

The composition, particularly the pharmaceutical composition according to the present invention can be used for various forms of administration, whereby local administration and systemic administration are particularly preferred. Even more preferred is a route of administration which is selected from the group comprising intramascular, percutaneous, subcutaneous, intravenous and pulmonary administration. As preferably used herein, local administration means that the respective composition is administered in close spatial relationship to the cell, tissue and organ, respectively, to which the composition and the biologically active compound, respectively, is to be administered. As used herein, systemic administration means an administration which is different from a local administration and more preferably is the administration into a body fluid such as blood and liquor, respectively, whereby the body liquid transports the composition to the cell, tissue and organ, respectively, to which the composition and the biologically active compound, respectively, is to be delivered.

As used herein, the cell across the cell membrane of which a biologically active compound is to be transferred by means of the compound and composition according to the present invention, respectively, is preferably an eukaryotic cell, more preferably a vertebrate cell and even more preferably a mammalian cell. Most preferably the cell is a human cell.

Any medicament which can be manufactured using the compound and composition according to the present invention, respectively, is for the treatment and prevention of a patient. Preferably such patient is a vertebrate, more preferably a mammal and even more preferably such mammal is selected from the group comprising mice, rats, dogs, cats, guinea pigs, rabbits, sheep, pigs, goats, cows, horses, poultry monkeys and humans. In a further aspect the compound and composition according to the present invention can be used as a transferring agent, more preferably as a transfection agent.

As preferably used herein a transferring agent is any agent which is suitable to transfer a compound, more preferably a biologically active compound such as a pharmaceutically active compound across a membrane, preferably a cell membrane and more preferably transfer such compound into a cell as previously described herein. Even more preferably, such transfer also comprises the release from any endosome/liposome.

In a still further aspect the present invention is related to a method for transferring, more particularly transfecting, a cell with a biologically active compound. In a first step, whereby the sequence of steps is not necessarily limited and in particular not limited to the sequence of steps outlined in the following, the cell and the membrane and cell, respectively, is provided. In a second step, a compound according to the present invention is provided as well as a biologically active compound such as a pharmaceutically active compound. This reaction can be contacted with the cell and the membrane, respectively, and due to the biophysical characteristics of the compound and the composition according to the present invention, the biologically active compound will be transferred from one side of the membrane to the other one, or in case the membrane forms a cell, from outside the cell to within the cell. It is within the present invention that prior to contacting the cell and the membrane, respectively, the biologically active compound and the compound according to the present invention, i.e. the cationic lipid, are contacted, whereupon preferably a complex is formed and such complex is contacted with the cell and the membrane, respectively.

In a further aspect of the present invention the method for transferring a biologically active compound and a pharmaceutically active compound, respectively, comprises the steps of providing the cell and the membrane, respectively, providing a composition according to the present invention and contacting both the composition and the cell and the membrane, respectively. It is within the present invention that the composition may be formed prior or during the contacting with the cell and the membrane, respectively.

In an embodiment of any method for transferring a biologically active compound as disclosed herein, the method may comprise further steps, preferably the step of detecting whether the biologically active compound has been transferred. Such detection reaction strongly depends on the kind of biologically active compounds transferred according to the method and will be readily obvious for the ones skilled in the art. It is within the present invention that such method is performed on any cell, tissue, organ and organism as described herein.

It is to be acknowledged that in a further embodiment the shielding agent is attached, as described herein, to the lipid component of the lipid composition according to the present invention, preferably to the cationic lipid.

The present invention is further illustrated by reference to the following figures and examples from which further features, embodiments and advantages of the present invention may be taken. More particularly, FIG. 1 shows the basic design of the cationic lipid according to the present invention;

FIG. 2 shows the synthesis of N-oleyl-palmitylamine which is a possible starting material for the synthesis of the compounds according to the present invention, whereby such synthesis is the one according to the prior art as described in U.S. Pat. No. 6,395,713;

FIG. 11 depicts an alternative synthetic route for the synthesis of beta-arginyl-2,3-diaminopropionic acid-N-palmityl-N-oleyl-amide trihydrochloride;

EXAMPLE 1

Synthesis of N-oleyl-palmityl Amine According to the prior art

N-oleyl-palmityl amine is an important starting material for the compounds according to the present invention. The N-oleyl-palmityl amine can, in principle, be synthesised as described in U.S. Pat. No. 6,395,713. The respective reaction scheme is depicted in FIG. 2. However, the starting material is oleyl amine of technical grade as provided by, e.g., Fluka. An analysis of this starting material by gas chromatography shows a purity of ≥70%, whereby 30% of the material consist of amine having different chain lengths. The reason for this could be that the material as such is obtained from plant sources. Combining both oleyl amine and 1-bromohexadecane (palmitylbromid) yields N-oleyl-palmityl amine after reacting both starting materials at 100 to 120° C. for 30 minutes. The yield is about 83%.

EXAMPLE 2

Synthesis of N-palmityl-oleyl Amine According to the Present Invention

Figure 1:
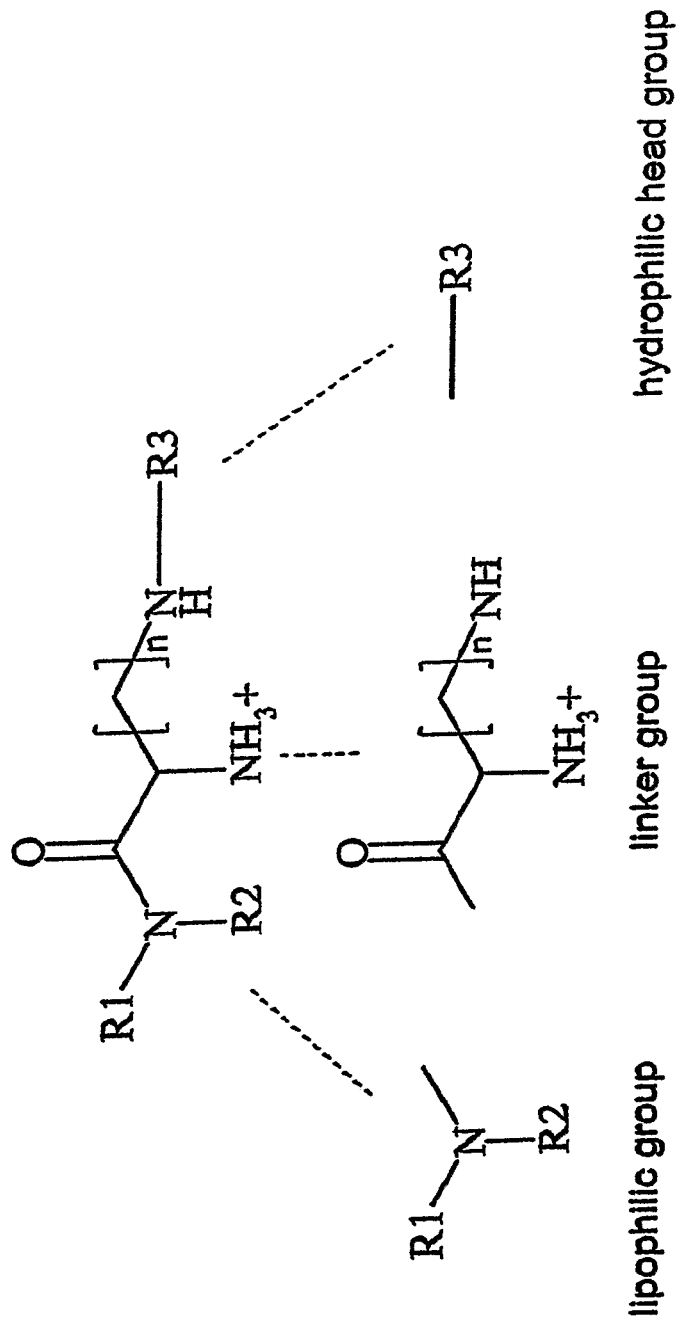
Figure 3:
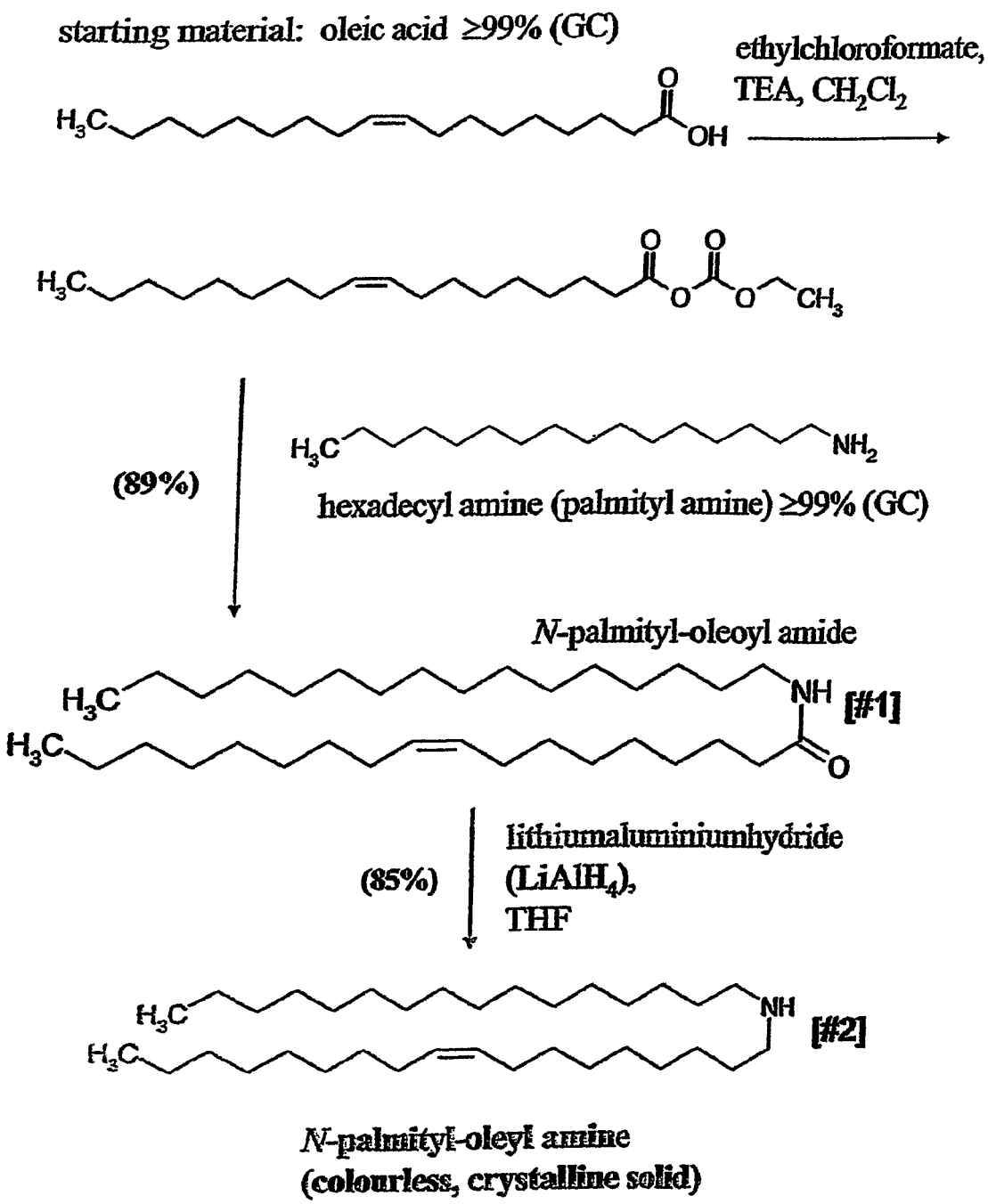
FIG. 3 depicts the synthesis of N-oleyl-palmitylamine which is an important starting material according to the present invention.

A new synthesis has been perceived by the present inventor in connection with the compounds according to the present invention (FIG. 3). This new reaction scheme is based on the finding of the present inventor that the high amount of impurities is affecting the quality of the transferring agent prepared based on this starting material. Accordingly, the reaction starts using oleic acid having a purity of ≥99% as shown by gas chromatography and contacting such oleic acid with ethylchloroformate, TEA and $CH_2Cl_2$ and reacting the thus obtained mixed carboxylic-carbonic anhydride with hexadecylamine (palmitylamine) having again a purity of 99% as shown by gas chromatography. The reaction product N-palmityl-oleoyl amide [#1] is subsequently reacted with $LiAlH_4$ (in THF) resulting in 85% N-palmityl-oleyl amine [#2] which is present as a colourless crystalline solid.

The more detailed reaction conditions are outlined in the following.

Synthesis of N-palmityl-oleoyl amide [#1]

2.62 ml (27.5 mmol) chloroformic acid ethyl ester are dissolved in 30 ml anhydrous dichloromethane in a 250 ml nitrogen flask according to Schlenk under argon inert gas and cooled to 0° C. A solution of 7.93 ml (25 mmol) oleic acid and 4.16 ml (30 mmol) triethylamine in 40 ml anhydrous dichloromethane are added dropwise under steering within 20 minutes. After steering on the ice bath for 30 minutes a solution of 6.64 g (27.5 mmol) palmitylamine in 50 ml $CHCl_3$ is rapidly added dropwise and the mixture is steered at room temperature for 2 hours. Subsequently, the solution is washed three times with 40 ml water each, the organic phase dried over $Na_2SO_4$ and the solvent removed using a rotary evaporator. The residue is re-crystallised from 100 ml acetone. 11.25 g (22.3 mmol) corresponding to a yield of 89% of a colourless solid is obtained.

Synthesis of N-palmityl-oleylamine [#2]

20 ml 1M $LiAlH_4$ in ether are provided under argon inert gas in a 250 ml three-neck flask having a dropping funnel and a reflux condenser and subsequently a solution of 7.59 g (15 mmol) palmityloleoylamide in 80 ml THE added dropwise within 20 minutes. The mixture is refluxed for 2.5 hours, then another 5 ml 1 M $LiAlH_4$ in ether is added and refluxed for another 2.5 hours. Excess hydride is decomposed using 6 M NaOH under ice bath cooling and the precipitate is filtered off. The precipitate is extracted twice with 40 ml of hot MtBE each, the combined organic phases dried over $Na_2SO_4$ and the solvent removed using a rotary evaporator. The residue is crystallised from 100 ml MtBE at −20° C. 6.23 g (12.7 mmol) corresponding to a yield of 85% of a colourless crystalline solid are obtained.

EXAMPLE 3

Synthesis of Boc-Dap(Fmoc)-N-plamityl-N-oleyl-amide [#3]

Figure 4:
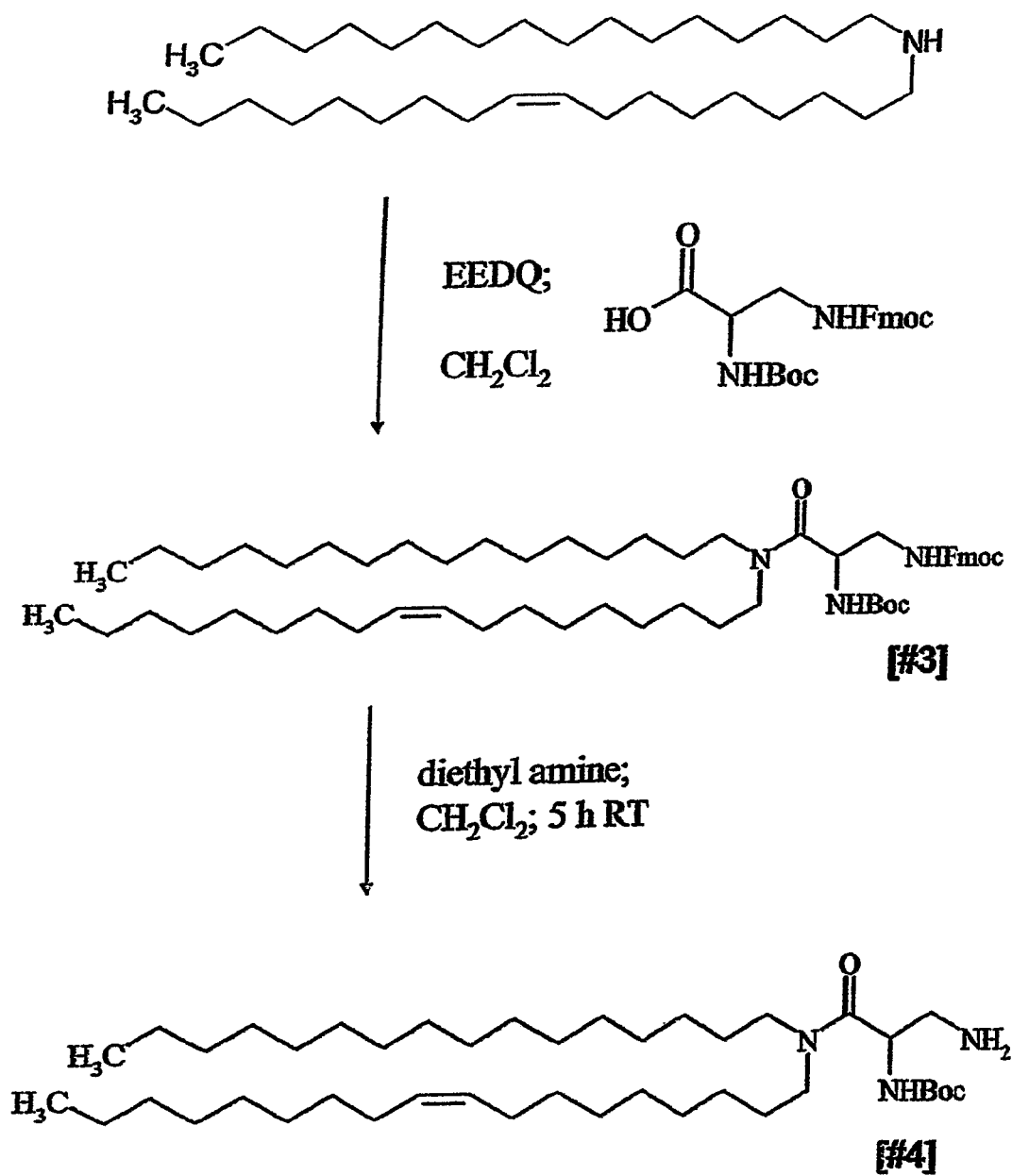
FIGS. 4-9 depict the synthesis of β-arginyl-2,3-amino propionic acid-N-palmityl-N-oleyl-amide trihyrdochloride, β-arginyl-2,3-diamino propionic acid-N-lauryl-N-myristyl-amide trihydrochloride and ε-arginyl-lysine-N-lauryl-N-myristyl-amide trihydrochloride.

521 mg (1.06 mmol) N-oleyl-palmitylamine in 10 ml anhydrous dichloromethane are dissolved in a 50 ml round-bottom flask and 289 mg (1.17 mmol) EEDQ are added. Subsequently, 500 mg (1.17 mmol) Boc-Dap(Fmoc)-OH are added under steering and the mixture is steered at room temperature for 20 hours. The solution is transferred with 80 ml dichloromethane into a separating funnel and washed three times with 20 ml 0.1 N HCl each and once with 20 ml saturated $NaHCO_3$ solution. After drying over $Na_2SO_4$ the solvent is removed using a rotary evaporator (FIG. 4). A yellowish viscous oil is obtained which is not further purified. In thin layer chromatography using hexane/ethylacetate of 1:1 a $R_f$ of 0.70 was observed.

EXAMPLE 4

Synthesis of Boc-Dap-N-palmityl-N-oleyl-amide [#4]

1 g Boc-Dap(Fmoc)-N-palmityl-N-oleyl-amide raw product were dissolved in 8 ml anhydrous dichloromethane in a 50 ml round-bottom flask. 3 ml diethylamine were added and steered at room temperature (FIG. 4). Thin layer chromatography control of the reaction showed that after 4.5 hours the reaction of the starting product was completed. The volatile components were removed by a rotary evaporator and the residue is chromatography purified using 40 g silica gel 60 (Merck) using hexane/ethylacetate 5:1. The product was eluted using a step gradient consisting of ethylacetate, ethylacetate/methanol 4:1 and dichloromethane/methanol 4:1. 576 mg (0.85 mmol) Boc-Dap-N-palmityl-N-oleyl-amide were obtained as a yellow viscous oil.

EXAMPLE 5

Synthesis of tetra-Boc-[β-arginyl-2,3-diaminopropionic acid-N-palmityl-N-oleyl-amide] [#5]

Figure 5:
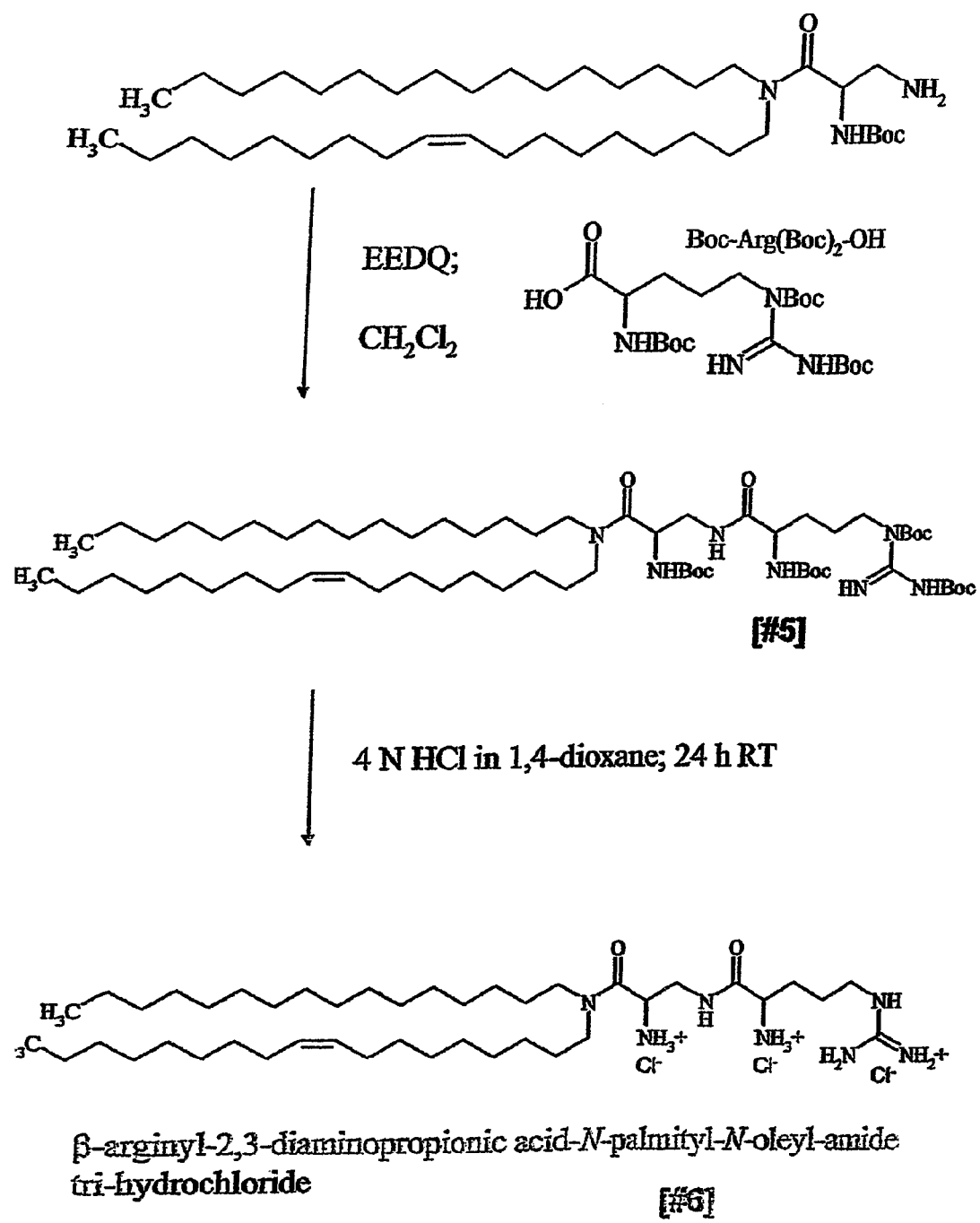

576 mg (0.85 mmol) Boc-Dap-N-palmityl-N-oleyl-amide were dissolved in 10 ml anhydrous dichloromethane in a 100 ml round-bottom flask and 210 mg (0.85 mmol) EEDQ and 403 mg (0.85 mmol) Boc-Arg(Boc)$_2$—OH were added under steering (FIG. 5). The mixture was steered under argon atmosphere at room temperature for 20 hours. Subsequently, the dichloromethane is removed by a rotary evaporator and the residue in 100 ml MtBE transferred into a separating funnel. The organic phase was thoroughly washed with 0.1 N HCl, 1 N NaOH and saturated NaHCO$_3$ solution, dried over Na$_2$SO$_4$ and the solvent removed by a rotary evaporator. The raw product was subsequently purified by flash chromatography (Combiflash Retrieve; Isco Inc.) using hexane/ethylacetate as eluent. 694 mg (0.61 mmol) corresponding to a yield of 72% of a colourless viscous oil was obtained.

EXAMPLE 6

Synthesis of β-arginyl-2,3-diaminopropionic acid-N-palmityl-N-oleyl-amide trihydrochloride [#6]

694 mg (0.61 mmol) well dried tetra-Boc-[β-arginyl-2,3-diaminopropionic acid-N-palmityl-N-oleyl-amide] were provided under argon atmosphere in a 25 ml nitrogen flask according to Schlenk and 8 ml 4N HCl in dioxane added (FIG. 5). The mixture was steered under argon inert gas at room temperature for 24 hours, whereby product precipitated as amorphous and partially as wax-like solid from the solution after about 6 to 8 hours. After completion of the reaction (thin layer control using CHCl$_3$/MeOH/NH$_4$OH 65:25:4) any volatile components were removed under high vacuum. 489 mg (0.58 mmol) β-arginyl-2,3-diaminopropionic acid-N-pamityl-N-oleyl-amide were obtained as trihydrochloride.

EXAMPLE 7

Synthesis of N-lauryl-myristyl amine [#7]

Figure 6:
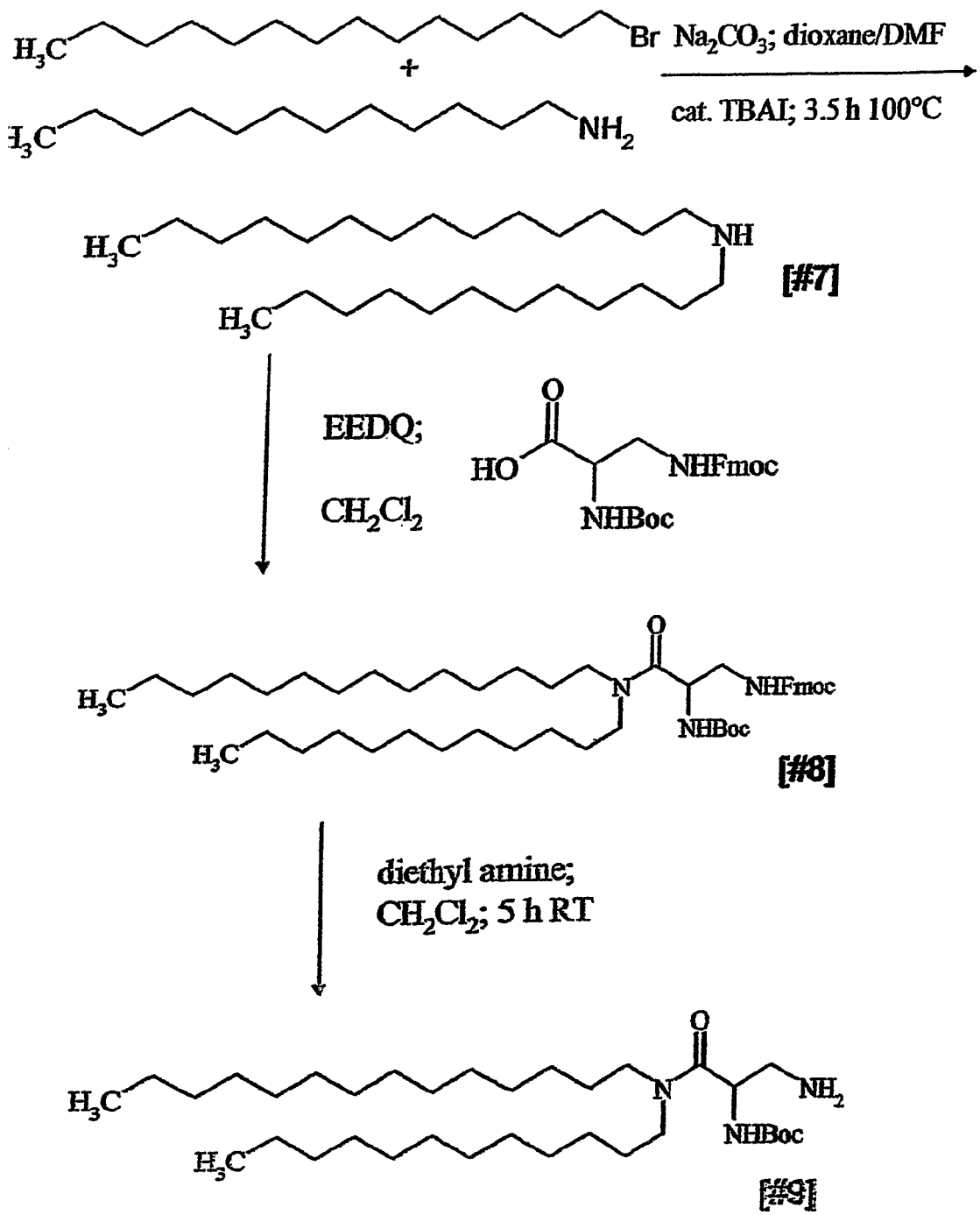

18.54 g (100 mmol) dodecylamine (laurylamine), 6.36 g (60 mmol) Na$_2$CO$_3$ and 50 mg tetrabutyl ammonium iodide (TBAI) were suspended in 100 ml anhydrous DMF in a 500 ml 3-neck flask having a reflux condenser and a dropping funnel. A solution of 16.4 ml (60 mmol) 1-bromo tetradecane in 100 ml anhydrous dioxane were added dropwise at 100° C. over a period of 110 minutes and the mixture was steered for another 3.5 hours at 100° C. (FIG. 6). The solution was filtered at a temperature as hot as possible. The crystalline solid which precipitated at 4° C. over night, was removed and was washed with a little of cold methanol. Subsequently, the solid was re-crystallised from 200 ml methanol. 9 g of colourless leaf-like crystals were obtained which are re-crystallised from 100 ml MtBE. The crystals which precipitated at −18° C., were sucked off from a cooled frit and washed with cold MtBE. 7.94 g (21 mmol) of a colourless crystalline solid were obtained, corresponding to a yield of 35%.

EXAMPLE 8

Synthesis of Boc-Dap(Fmoc)-N-laurel-N-myristyl amide [#8]

715 mg (1.68 mmol) Boc-Dap(Fmoc)-OH were dissolved in 15 ml anhydrous dichloromethane in a 50 ml round-bottom flask and 420 mg (1.7 mmol) EEDQ were added. The mixture was steered at room temperature for 45 minutes and subsequently a solution of 641 mg (1.68 mmol) N-lauryl-myristyl amine in 25 ml anhydrous dichloromethane was slowly added dropwise within 60 minutes (FIG. 6). After a reaction time of 20 hours the solvent was removed by a rotary evaporator and the residue transferred with 100 ml MtBE into a separating funnel. The solution was thoroughly washed with 0.1 N HCl and saturated NaHCO$_3$ solution, the organic phase dried over Na$_2$SO$_4$ and the solvent removed by a rotary evaporator. 1.02 g of a raw product were obtained which was purified by flash chromatography (Combiflash Retrieve; Isco Inc.) using hexane/ethylacetate as eluent. 607 mg pure product were obtained as colourless, very viscous oil. Thin layer chromatography using hexane/ethylacetate 1:1 provided a R$_f$ of 0.58.

EXAMPLE 9

Synthesis of Boc-Dap-N-lauryl-N-myristyl amide [#9]

607 mg Boc-Dap(Fmoc)-N-lauryl-N-myristyl amide were dissolved in 8 ml anhydrous dichloromethane in a 50 ml round-bottom flask (FIG. 6). 3 ml diethylamine were added and the reaction steered at room temperature for 4.5 hours. The volatile constituents were removed using a rotary evaporator and the residue was purified by chromatography using 40 g silica gel 60 (Merck) with hexane/ethylacetate 5:1. The product was eluted by a step gradient consisting of ethylacetate, dichloromethane and dichloromethane/methanol 3:1. 372 mg (0.655 mmol) Boc-Dap-N-lauryl-N-myristyl amide were obtained as yellowish, viscous oil.

EXAMPLE 10

Synthesis of tetra-Boc-[β-arginyl-2,3-diaminopropionic acid-N-lauryl-N-myristyl amide] [#10]

Figure 7:
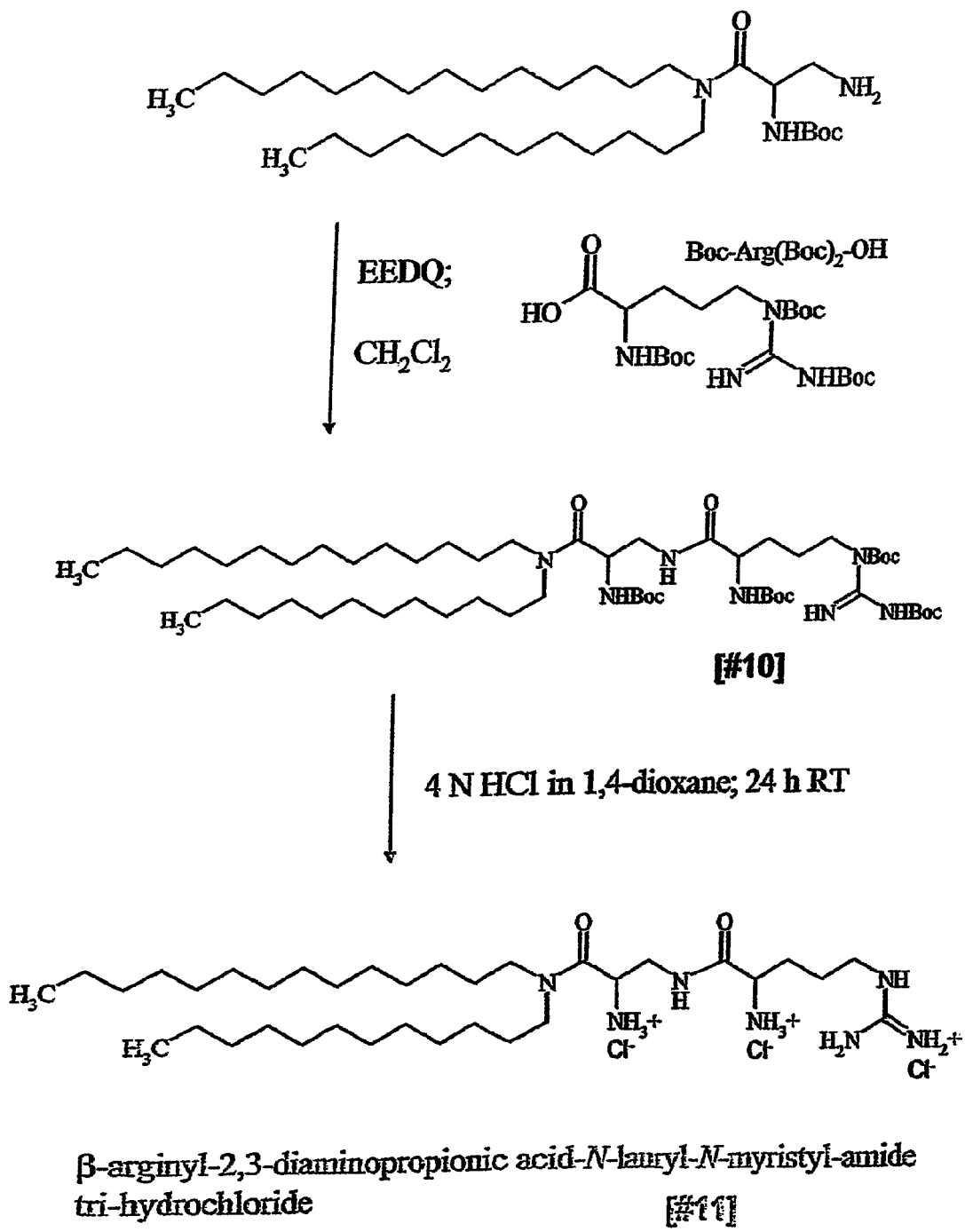

372 mg (0.655 mmol) Boc-Dap-N-lauryl-N-myristyl amide were dissolved in 8 ml anhydrous dichloromethane in a 50 ml round-bottom flask and 162 mg (0.655 mmol) EEDQ and 311 mg (0.655 mmol) Boc-Arg-(Boc)$_2$—OH were added under steering (FIG. 7). The mixture was steered at room temperature for 20 hours. Subsequently, the dichloromethane was removed using a rotary evaporator and the residue was transferred with 80 ml MtBE into a separating funnel. The organic phase was thoroughly washed with 0.1 N HCl, 1 N NaOH and saturated NaHCO$_3$ solution, dried over Na$_2$SO$_4$ and the solvent removed by a rotary evaporator. The raw product was subsequently purified by flash chromatography (Combiflash Retrieve; Isco Inc.) using a step gradient of hexane/ethylacetate. 500 mg (0.5 mmol) of a colourless viscous oil were obtained, corresponding to a yield of 76%.

EXAMPLE 11

Synthesis of β-arginyl-2,3-diaminopropionic acid-N-lauryl-N-myristyl amide trihydrochloride [#11]

511 mg (0.5 mmol) well dried tetra-Boc-[β-arginyl-2,3-diaminopropionic acid-N-lauryl-N-myristyl amide] were provided under argon in a 25 ml argon flask according to Schienk and 10 ml 4 N HCl in dioxane were added (FIG. 7). The mixture was steered under argon inert gas at room temperature for 24 hours, whereby product precipitated as partially amorphous, partially wax-like solid from the solution after 6 to 8 hours. Upon completion of the reaction (thin layer chromatography control using CHCl$_3$/MeOH/NH$_4$OH 65:25:4) all volatile components were removed under high vacuum. 323 mg (0.5 mmol) β-arginyl-2,3-diaminopropionic acid-N-lauryl-N-myristyl amide in the form of the tri-hydrochloride were obtained.

EXAMPLE 12

Synthesis of Boc-Lys(Fmoc)-N-laurel-N-myristyl amide [#12]

Figure 8:
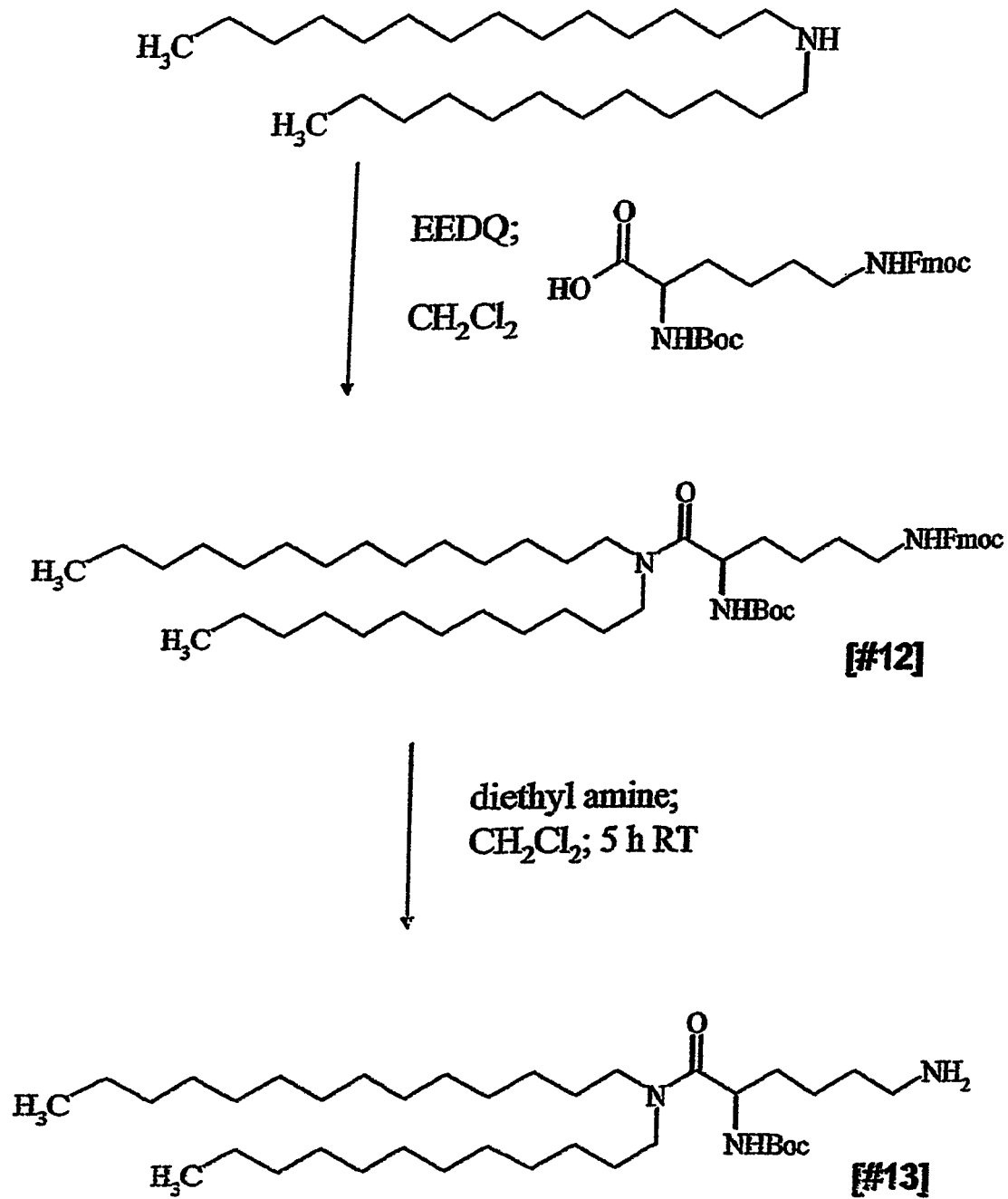

937 mg (2 mmol) Boc-Lys(Fmoc)-OH were dissolved in 10 ml anhydrous dichloromethane in a 50 ml round-bottom flask and 495 mg (2 mmol) EEDQ were added (FIG. 8). The mixture was steered at room temperature for 60 minutes and subsequently a solution of 764 mg (2 mmol) N-laurly-myristyl amine in 30 nil anhydrous dichloromethane was slowly added in a dropwise manner within 120 minutes. After a reaction time of 20 hours the solvent was removed using a rotary evaporator and the residue transferred with 100 ml MtBE into a separating funnel. The solution was thoroughly washed with 0.1 N HCl and saturated NaHCO$_3$, the organic phase dried over Na$_2$SO$_4$ and the solvent removed using a rotary evaporator. 1.757 g of a raw product were obtained which was purified using flash chromatography with hexane/ethylacetate 4:1 as eluent. 1.377 g pure product is obtained as colourless, very viscous oil. Thin layer chromatography using hexane/ethylacetate 1:1 gave a R$_f$ of 0.57.

EXAMPLE 13

Synthesis of Boc-Lys-N-lauryl-N-myristyl amide [#13]

1.377 g Boc-Lys(Fmoc)-N-lauryl-N-myristyl-amide were dissolved in 16 ml anhydrous dichloromethane in a 50 ml round-bottom flask. 6 ml diethylamine were added and the mixture was steered at room temperature for 5 hours (FIG. 8). The volatile components were removed using a rotary evaporator and the residue was purified by chromatography using 40 g silica gel 60 (Merck) with hexane/ethylacetate 5:1. The product was eluted using a step gradient consisting of ethylacetate, dichloromethane and dichloromethane/methanol 3:1. 556 mg (0.911 mmol) Boc-Lys-N-lauryl-N-myristyl amide were obtained as yellowish viscous oil as well as 119 mg of a mixed fraction.

EXAMPLE 14

Synthesis of tetra-Boc-[ε-arginyl-lysine-N-lauryl-N-myristyl amide] [#14]

Figure 9:
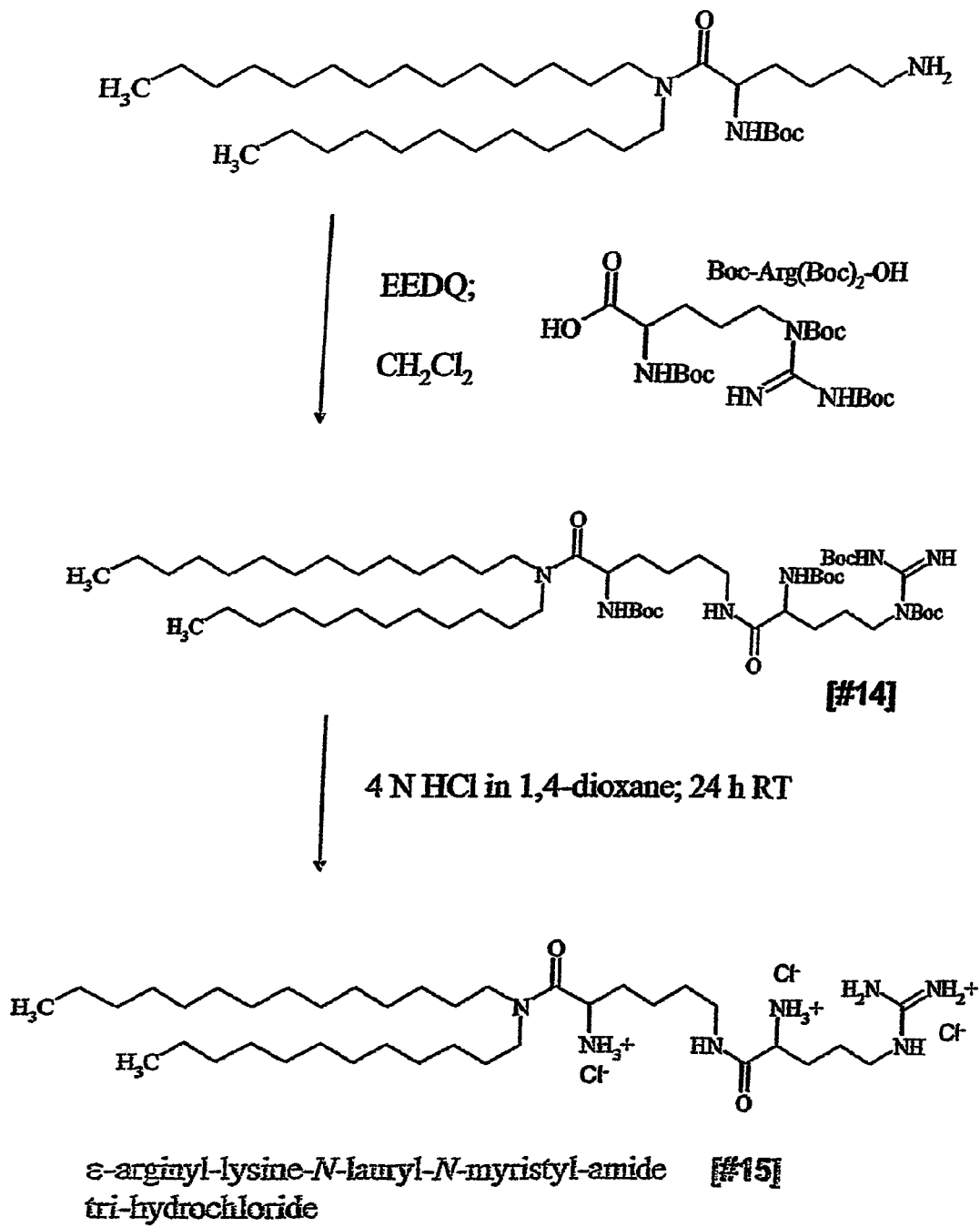

556 mg (0.911 mmol) Boc-Lys-N-lauryl-N-myristyl-amide were dissolved in 40 ml anhydrous dichloromethane and 226 mg (0.911 mmol) EEDQ and 433 mg (0.911 mmol) Boc-Arg(Boc)$_2$—OH were added under steering (FIG. 9). The mixture was steered at room temperature for 20 hours. Subsequently, the dichloromethane was removed using a rotary evaporator and the residue was transferred with 80 ml MtBE into a separating funnel. The organic phase was thoroughly washed with 0.1 N HCl and saturated NaHCO$_3$ solution, dried over Na$_2$SO$_4$ and the solvent removed using a rotary evaporator. The raw product was subsequently purified by flash chromatography (Combiflash Retrieve; Isco Inc.) using a hexane/ethylacetate step gradient. A colourless, viscous oil was obtained with a yield of 730 mg (0.684 mmol) corresponding to 75%.

EXAMPLE 15

Synthesis of ε-arginyl-lysine-N-laurel-N-myristyl amide trihydrochloride 730 mg (0.684 mmol) well dried tetra-Boc-[ε-arginyl-lysin-N-laurly-N-myristyl amide] were provided under argon in a 25 ml argon flask according to Schlenk and 10 ml 4 N HCl in dioxane were added (FIG. 9). The mixture was steered under argon inert gas at room temperature for 24 hours, whereupon product precipitated from the solution as an amorphous, partially wax-like solid after about 8 hours. Upon completion of the reaction such as controlled by thin layer chromatography using CHCl$_3$/MeOH/NH$_4$OH 65:25:4, all volatile components were removed under high vacuum. 491 mg (0.633 mmol) ε-arginyl-lysin-N-laurly-N-myristyl amide were obtained as tihydrochloride.

EXAMPLE 16

Synthesis of Tri-Boc-γ-carbamidino-α,γ-diamino butyric acid [#16]

Figure 10:
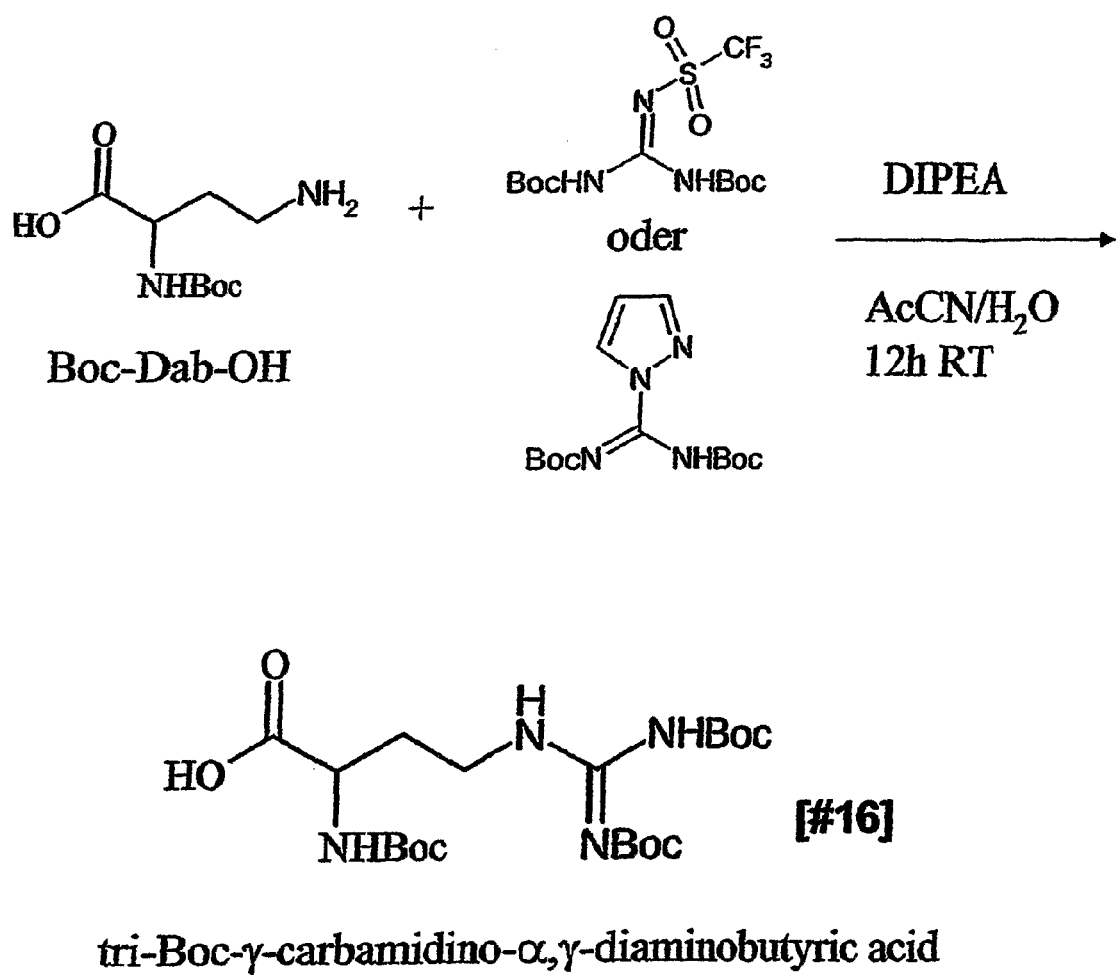
FIG. 10 depicts the synthesis of an alternate cationic head group which is an alternative component for the synthesis of the cationic lipids according to the present invention.

1.31 g (6 mmol) Boc-Dab-OH were provided in 15 ml acetonitrile in a 100 ml round-bottom flask and 12 mmol diisopropylethyl amine (DIPEA) were added (FIG. 10). Subsequently water was added dropwise until a part of the Boc-Dab-OH dissolved and subsequently 1.96 g (5 mmol) 1,3-di-Boc-2-(trifluoromethylsulfonyl)guanidine were added. The mixture was steered at room temperature for 12 hours, whereupon the acetonitrile was removed using a rotary evaporator. The aqueous residue was diluted with 5 ml water and 50 ml dichloromethane were added. The reaction is acidified to a pH 2 by adding 2 N HCl under steering and subsequent separation of the organic phase. The aqueous phase was extracted with 50 ml dichloromethane and the combined organic phases were subsequently washed with some of diluted HCl and saturated NaCl solution. The organic phase was dried over Na$_2$SO$_4$ and the solvent was removed using a rotary evaporator. The residue was purified using chromatography on silica gel 60 using hexane/ethylacetate 2:1. 1.138 g (2.47 mmol), corresponding to a yield of 50%, of a colourless amorphous solid was obtained.

EXAMPLE 17

Synthesis of beta-arginyl-2,3-diaminopropionic acid-M-palmityl-N-oleyl-amide trihydrochloride [##6]

1.225 g (6 mmole) BOC-Dap-OH in 15 ml absolute CH2Cl2 are suspended in a 250 ml Schlenk flask comprising a dropping funnel under an argon atmosphere and 1.72 ml trimethylamine are added. A solution of 1.52 ml (12 mmole) TMSCl in 30 ml absolute CH2Cl2 is added dropwise within 15 to 20 minutes at room temperature under vigorous stirring. In the meantime 941 mg (5.8 mmole) carbonyl diimidazole is dissolved in 8 ml absolute CH2Cl2 in a 100 ml Schlenk flask under argon atmosphere. A solution of 2.66 g (5.6 mmole) Boc-Arg(Boc)2-OH in 25 ml absolute CH2Cl2 is added dropwise within 15 to 20 minutes at room temperature and under stirring. Both reaction solutions are stirred at room temperature for 4 h. Subsequently, 832 μl (6 mmole) triethyl amine are added to the first solution and the second solution is added dropwise within 15 to 20 minutes through the dropping funnel at room temperature under argon atmosphere. After 15 to 20 minutes 30 ml water are added, vigorously stirred for 45 minutes and the solution is adjusted to a pH of 2. The organic phase is separated and the aqueous phase extracted several times with CH2Cl2. The combined organic phases are dried with a saturated solution of NaCl and sodium sulfate and the solvent removed using a rotary evaporator. The glass-like residue is purified using flash chromatography on silicagel using dichloromethane as eluent. 2.74 g (4.15 mmole; 74%) of a colourless, amorphous solid is obtained [compound 17].

This solid is reacted with oleyl palmityl amine [#2] under conditions which are essentially analogous to the one of Example 10, whereby the temperature is set to 35 to 40° C. (yield 72%). The intended final product β-arginyl-2,3-diaminopropionic acid-N-palmityl-N-oleyl-amide trihydrochloride [#6] is obtained upon cleaving off the Boc protection groups as described in Example 11. The thus obtained product can be further purified using flash chromatography on RP-18 silica gel using MeOH/water as eluent.

EXAMPLE 18

Manufacture of Complexes Consisting of Cationic Liposomes and siRNA (Lipoplexes)

Lipoplexes consisting of cationic liposomes and siRNA were manufactured using standard technologies known in the art such as lipid film/cake, ethanole injection procedure, reversed phase evaporation and detergent dialysis procedure [c.f. Liposomes as Tools in Basic Research and Industry; Jean R. Philippot and Francis Schuber; CRC Press January 1995 and Liposome Technology: Preparation of Liposomes:001 Gregory Gregoriadis CRC Press I Llc. April 1984].

The thus obtained liposomes which are also referred to herein as lipoplexes comprise as the lipid beta-arginyl-2,3-diaminopropionic acid-N-palmityl-N-oleyl-amide trihydrochloride and additionally either 1,2-diphytanoyl-sn-glycero-3-phosphoethanolamine or 1,2-dioleyl-sn-glycero-3-phosphoethanolamine, whereby the use of 1,2-diphytanoyl-sn-glycero-3-phosphoethanolamine is preferred. The lipid fraction of such liposomes and lipoplexes, respectively, was 50 mol % beta-arginyl-2,3-diaminopropionic acid-N-palmityl-N-oleyl-amide trihydrochloride and either 50 mol % 1,2-diphytanoyl-sn-glycero-3-phosphoethanolamine or 50 mol % 1,2-dioleyl-sn-glycero-3-phosphoethanolamine.

The combination of 50 mol % β-arginyl-2,3-diaminopropionic acid-N-palmityl-N-oleyl-amide trihydrochloride and 50 mol % 1,2-diphytanoyl-sn-glycero-3-phosphoethanolamine is also referred to herein as atuFect.

It is to be understood that in principle any other lipid and lipid composition as disclosed herein can be manufactured using the previously mentioned techniques as well as the further processing steps.

The liposomes and lipoplexes, respectively, are subjected to further processing steps so as to trim them with regard to size, polydispersibility and layer design. These characteristics can be adjusted by sonication, extrusion such as through porous membranes, and homogenisation, preferably high pressure homogenisation.

Figure 12A:
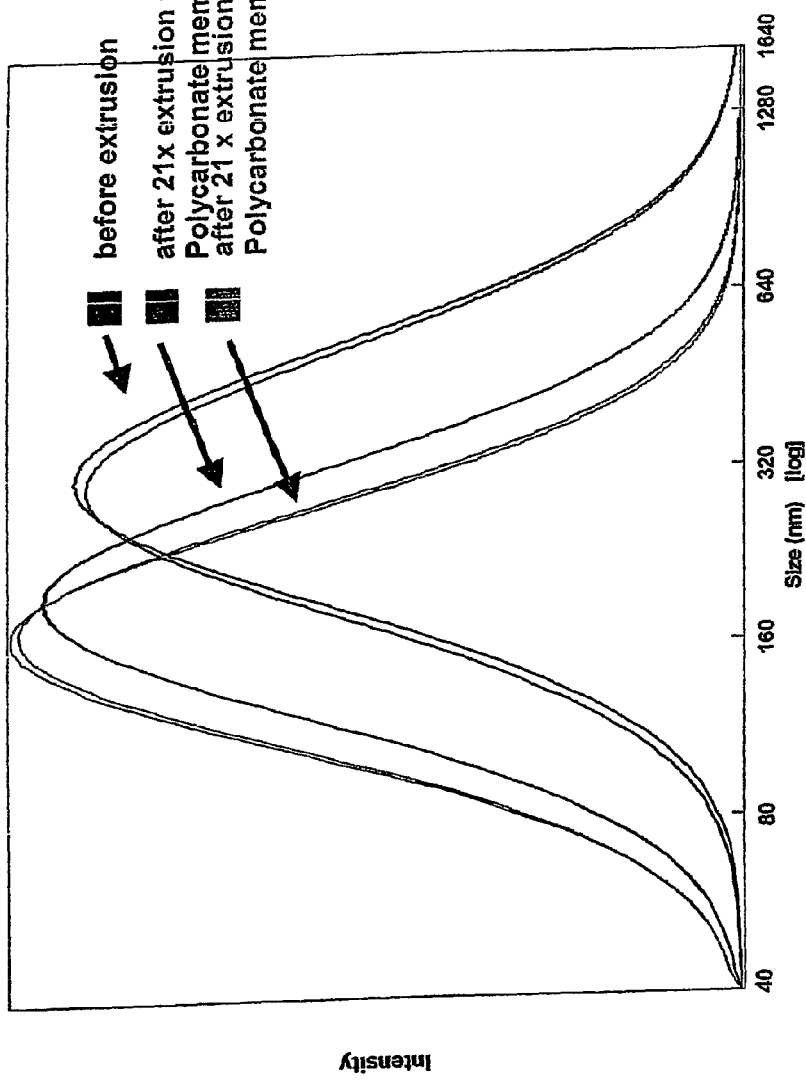
FIGS. 12A and 12B depict the size distribution of lipid formulations according to the present invention and the impact of extrusion and high-pressure homogenisation, respectively.
Figure 12B:
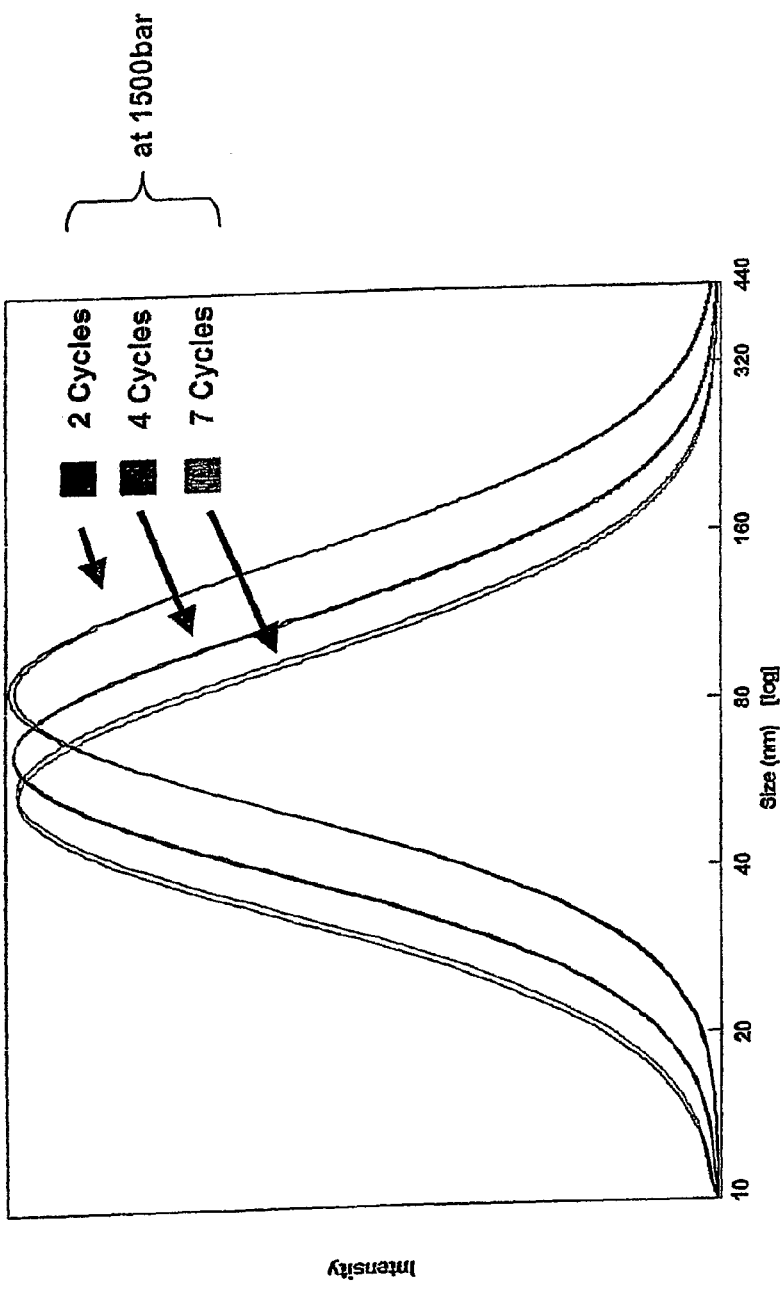

The thus formed liposomes were characterised by photon correlation spectroscopy with Beckman-Coulter N 5 submicron particle analyser and the results of such liposomes either sized by extrusion or by high-pressure homogenisation are depicted in FIGS. 12A and 12B, respectively.

From FIG. 12A it can be taken that the size distribution of the liposomes can be modified using different membranes having different size exclusions, in the present case 1,000 nm and 400 nm, respectively. In both cases, the extrusion step was repeated 21 times. It is, however, within the present invention that the size exclusion can be from about 50 to 5000 nm, and that the extrusion steps can be repeated 10 to 50 times.

As may be taken from FIG. 12B high-pressure homogenisation is also a suitable means to modify the size distribution of the liposomes, whereby upon applying such high-pressure homogenisation the size of the liposomes depends on the number of homogenisation cycles to which the liposomes were subjected. Typical pressure ranges are from 100-2500 bar, whereby in the present case the applied pressure was 1,500 bar.

EXAMPLE 19

Lipid Composition and PEG Content

In order to test the impact of PEG on the efficacy of transfection and delivery of lipid compositions comprising β-arginyl-2,3-diaminopropionic acid-N-palmityl-N-oleyl-amide trihydrochloride (cationic lipid) as the first lipid component, 1,2-diphytanoyl-sn-glycero-3-phosphoethanolamine (DPhyPE) as the first helper lipid and ceramide conjugated to PEG2000 (C8 mPEG2000) and PEG5000 (C8 mPEG5000), respectively, the following formulations were generated in accordance with the methods disclosed herein:

| $A_1$-$A_5$ formulations: | | | |
|---|---|---|---|
| | Cationic lipid [mol %] | DPhyPE [mol %] | C8mPEG2000 [mol %] |
| $A_1$ | 50 mol % | 49 | 1 |
| $A_2$ | 50 mol % | 47.5 | 2.5 |
| $A_3$ | 50 mol % | 45.0 | 5.0 |
| $A_4$ | 50 mol % | 42.5 | 7.5 |
| $A_5$ | 50 mol % | 40.0 | 10 |

| $B_1$-$B_5$ formulations: | | | |
|---|---|---|---|
| | Cationic lipid [mol %] | DPhyPE [mol %] | C8mPEG2000 [mol %] |
| $B_1$ | 49 | 50 mol % | 1 |
| $B_2$ | 47.5 | 50 mol % | 2.5 |
| $B_3$ | 45.0 | 50 mol % | 5.0 |
| $B_4$ | 42.5 | 50 mol % | 7.5 |
| $B_5$ | 40 | 50 mol % | 10.0 |

For any of the aforementioned formulations the lipid concentration was 1.445 mg/ml, siRNA concentration was 15 µM in 300 mM sucrose. Dilution of the concentrated stock-complexes formed yielded an end concentration of 20, 10, 5 nM siRNA in the cell culture medium.

The RNAi molecules contained in said formulations were directed against PTEN and the sequences were as follows: First strand having the following sequence: uaaguucuagcuguggugg-P (SEQ ID NO: 1); second strand having the sequence ccaccacagcuagaacuua-P (SEQ ID NO: 2), whereby the modification pattern is such that the nucleotides which are printed in bold and, are 2'-O-methyl nucleotides; at any of the strands, the 3' end starts with a phosphate depicted by P in the aforementioned sequences.

Figure 13A:
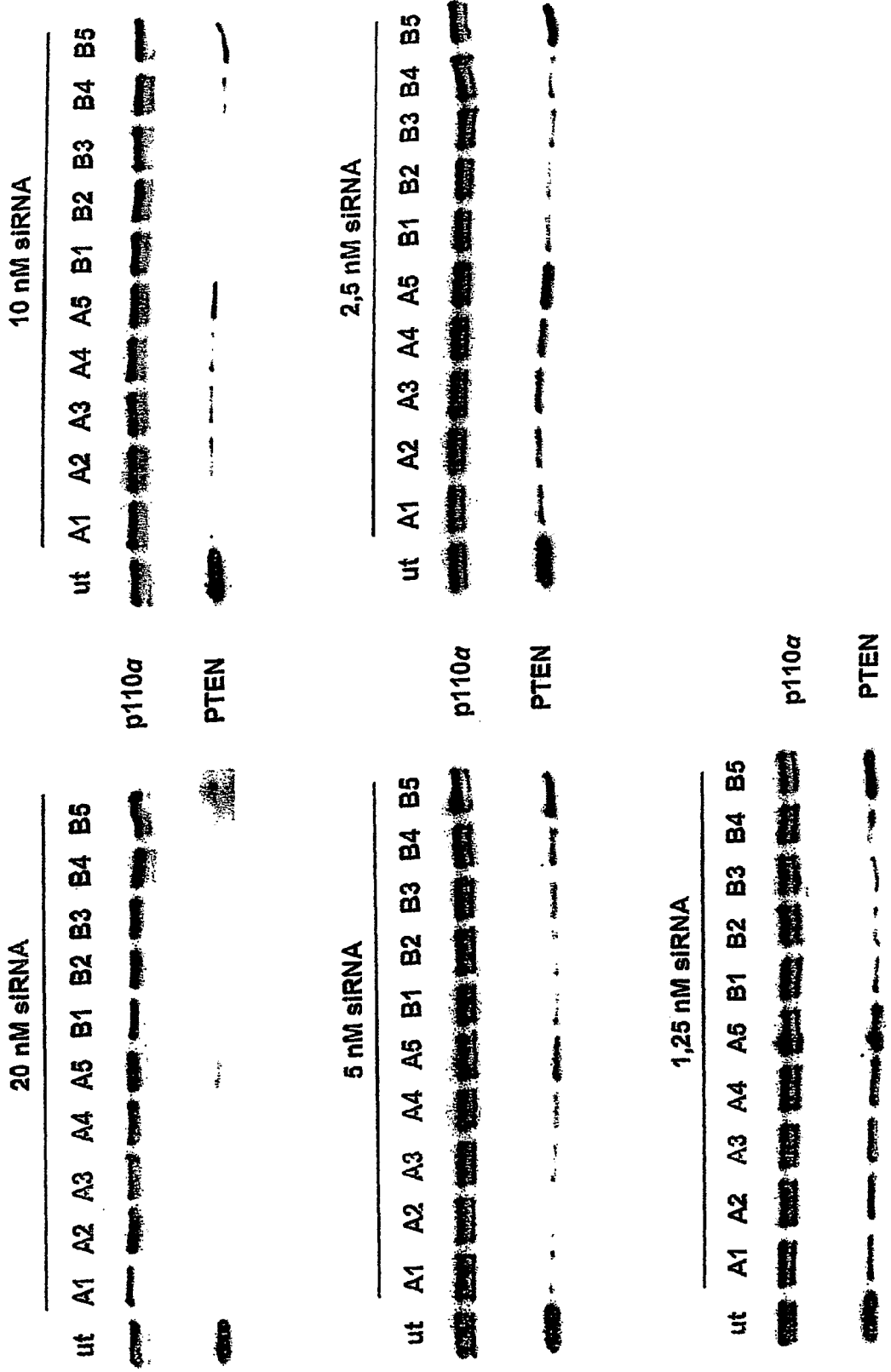
FIGS. 13A and 13B depicts the result of a Western Blot analysis and the impact of different concentrations of PEG-substituted lipids.
Figure 13B:
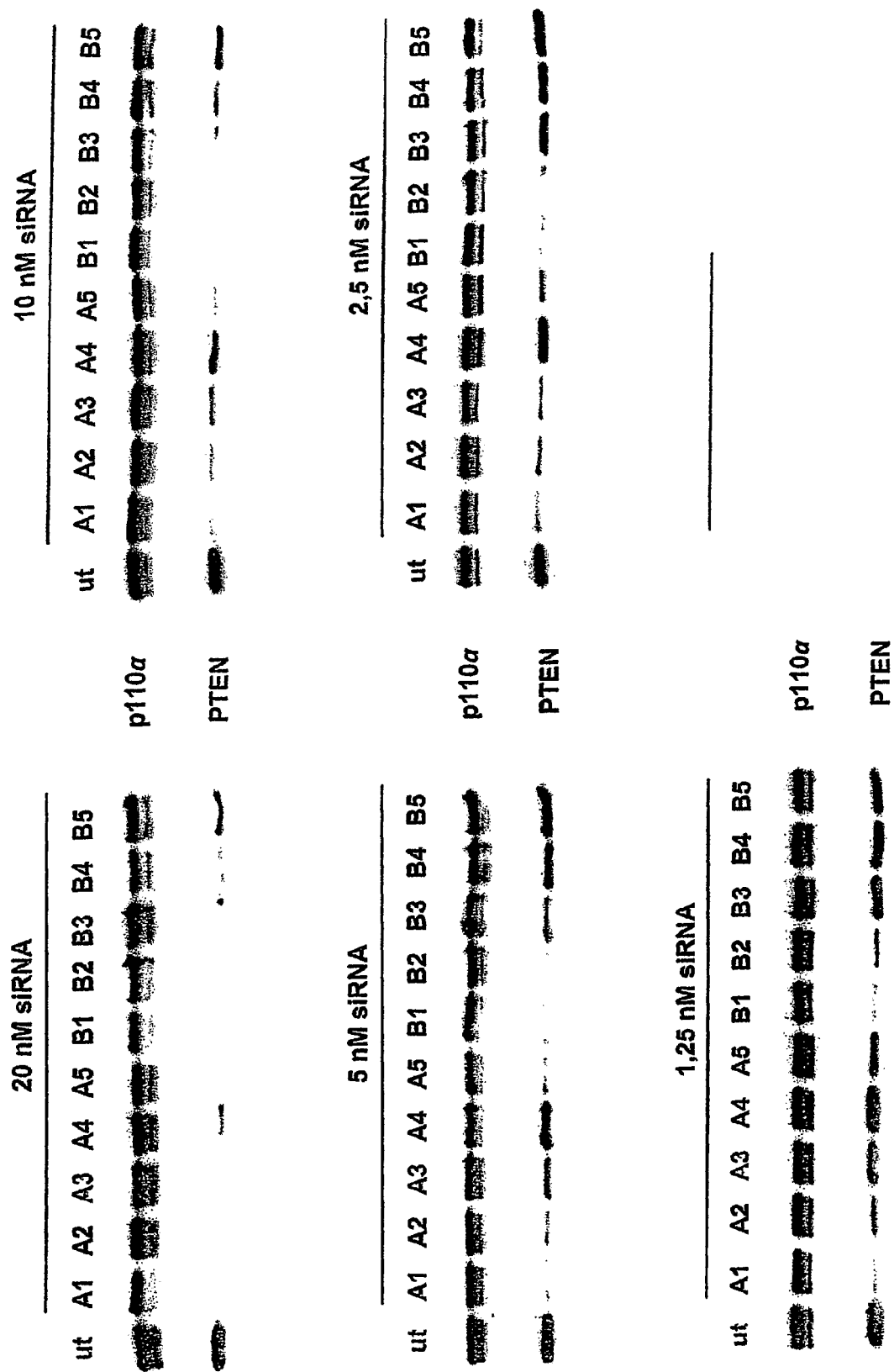

The lipid formulations were administered to HeLa cells contained in a 6 well plate each containing 40,000 cells/well. The cells were analysed for expression of PTEN and the results depicted in FIG. 13 as Western Blots. p110a expression was used as loading control and detected by an antibody. From any of the Western Blots depicted in FIGS. 13 A and 13B it can be taken that the content of the PEG compound, i.e. the shielding compound can be increased up to 5 and 7.5 mol %, whereby the concentration can be higher or be at the higher end of this range in case of PEG2000 compared to PEG5000 used.

This is a clear advantage compared to those PEG containing compositions where the PEG is not removable from the lipid composition. Lipid formulations of similar compositions comprising 1,2-distearoyl-sn-glycero-3-phosphoethanolamine-polyethylen-glycole (DSPE-PEG2000) in the range from 1 to 5 mol % rather than the ceramide PEG conjugate allow only the introduction of 1 to 2 mol % so as to provide for an efficient knockdown.

The features of the present invention disclosed in the specification, the claims and/or the drawings may both separately and in any combination thereof be material for realizing the invention in various forms thereof.

The invention claimed is:

1. A lipid composition comprising:
a cationic lipid component that is a compound according to formula (I),

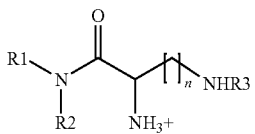

(I)

wherein $R_1$ and $R_2$ are each independently alkyl;
n is 1-4;
$R_3$ is acyl selected from the group consisting of lysyl, ornithyl, 2,4-diaminobutyryl, histidyl and an acyl moiety according to formula (II),

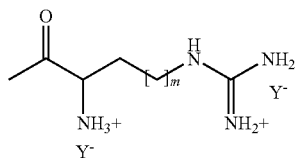

(II)

wherein m is any integer from 1 to 3,
wherein the $NH_3^+$ is optionally absent, and
$Y^-$ is a pharmaceutically acceptable anion,
a first helper lipid selected from a phospholipid or a steroid, and
a shielding compound comprising PEG, HEG, polyhydroxyethyl starch (polyHES) or polypropylene,
wherein said shielding compound provides for a prolonged circulation time in vivo of said lipid composition.

2. The lipid composition according to claim 1, wherein said shielding compound is PEG2000 or PEG5000.

3. The lipid composition according to claim 1, wherein said composition further comprises at least one component selected from the group consisting of a second helper lipid, a peptide, a protein, an oligonucleotide, a polynucleotide and a nucleic acid.

4. The composition according to claim 3 wherein the second helper lipid is a phospholipid or steroid.

5. The composition according to claim 4, wherein at least one of the first or second helper lipid is selected from the group consisting of 1,2-diphytanoyl-sn-glycero-3-phosphoethanolamine and 1,2-dioleyl-sn-glycero-3-phosphoethanolamine.

6. The composition according to claim 5, wherein the cationic lipid component is β-arginyl-2,3-diamino propionic acid-N-palmityl-N-oleyl-amidtrihydrochloride, and the first or second helper lipid is 1,2-diphytanoyl-sn-glycero-3-phosphoethanolamine.

7. The composition according to claim 6, wherein the cationic lipid component is 50 mol % and the first or second helper lipid is 50 mol % of the overall lipid content of the composition.

8. The composition according to claim 3, wherein the content of the first and/or second helper lipid is from about 20 mol % to about 80 mol % of the overall lipid content of the composition.

9. The composition according to claim 8, wherein the content of the first and/or second helper lipid is from about 35 mol % to about 65 mol % of the overall lipid content of the composition.

10. The composition according to claim 3, wherein at least the first or the second helper lipid is selected from the group consisting of a PEG moiety, a MEG moiety, a polyhydroxyethyl starch (polyHES) moiety and a polypropylene moiety, wherein said helper lipid moiety is from about 500 to 10000 Da.

11. The composition according to claim 10, wherein said lipid moiety is from about 2000 to 5000 Da.

12. The composition according to claim 10, wherein the helper lipid comprising the PEG moiety is selected from the group consisting of 1,2-distearoyl-sn-glycero-3-phosphoethanolamine and 1,2-dialkyl-sn-glycero-3-phosphoethanolamine.

13. The composition according to claim 12, wherein the PEG moiety has a molecular weight from 2,000 to 5,000 Da.

14. The composition according to claim 13, wherein the composition comprises β-arginyl-2,3-diamino propionic acid-N-palmityl-N-oleyl-amide trihydrochloride as the lipid component, 1,2-diphytanoyl-sn-glycero-3-phosphoethanolamine as a first helper lipid and 1,2-distearoyl-sn-glycero-3-phosphoethanolamine-PEG2000 as a second helper lipid.

15. The lipid composition according to claim 3, wherein said component is a nucleic acid.

16. The lipid composition according to claim 15, wherein said nucleic acid is selected from the group consisting of an RNAi, an siRNA, an siNA, an antisense nucleic acid, a ribozyme, an aptamer and a spiegelmer.

17. The lipid composition according to claim 15, wherein said shielding compound is covalently linked to said nucleic acid.

18. The lipid composition according to claim 17, wherein the linker moiety is selected from the group consisting of an ssRNA, an ssDNA, a dsRNA, a dsDNA, a peptide, an S—S-linker and a pH sensitive linker.

19. The lipid composition according to claim 17, wherein the nucleic acid is selected from the group consisting of RNAi, siRNA and siNA, and the linker is attached to the 3' end of the sense strand of said nucleic acid.

20. The lipid composition according to claim 1, wherein the shielding compound is a conjugate of PEG and ceramide.

21. The lipid composition according to claim 20, wherein the ceramide comprises at least one short carbon chain substituent of from 6 to 10 carbon atoms.

22. The composition according to claim 20, wherein the composition contains from about 1 to 10 mol % of the conjugate of PEG and the ceramide.

23. The composition according to claim 22, wherein the ceramide is C8m and the PEG is PEG 2000, and wherein the content of the conjugate of PEG and the ceramide is from about 1 to 7.5 mol %.

24. The composition according to claim 22, wherein the ceramide is C8m and PEG is PEG5000 and wherein the content of the conjugate of PEG and ceramide is from about 1 to 5 mol %.

25. The composition according to claim 22, wherein the content of the cationic lipid component is from about 42.5 mol % to 50 mol %, wherein the content of the first helper lipid is from about 42.5 to 50 mol %, and wherein the sum of the content of the lipid component, the first helper lipid, and the conjugate of PEG and ceramide is 100 mol %.

26. The lipid composition according to claim 1, wherein said first helper lipid is ceramide, and wherein said ceramide is conjugated to PEG.

27. The lipid composition according to claim 1, wherein said composition further comprises a second helper lipid, wherein said second helper lipid is ceramide, and wherein said ceramide is conjugated to PEG.

28. The lipid composition according to claim 1, wherein said shielding compound comprises a pH-sensitive linker.

29. The lipid composition according to claim 28, wherein said linker is an anionic linker.

30. The lipid composition according to claim 29, wherein said anionic linker is substantially neutral in an endosome.

31. The lipid composition according to claim 28, wherein the pH-sensitive linker is selected from the group consisting of oligo glutamic acid, an oligophenolate and diethylene triamine penta acetic acid.

32. The lipid composition according to claim 1, wherein $R_1$ and $R_2$ are each independently selected from the group consisting of lauryl, myristyl, palmityl and oleyl.

33. The lipid composition according to claim 1, wherein $R_1$ is lauryl and $R_2$ is myristyl, or $R_1$ is palmityl and $R_2$ is oleyl.

34. The lipid composition according to claim 1, wherein m is 1 or 2.

35. The lipid composition according to claim 1, wherein $Y^-$ is selected from the group consisting of halide, acetate and trifluoroacetate.

36. The lipid composition according to claim 1, wherein said cationic lipid component is selected from the group consisting of:

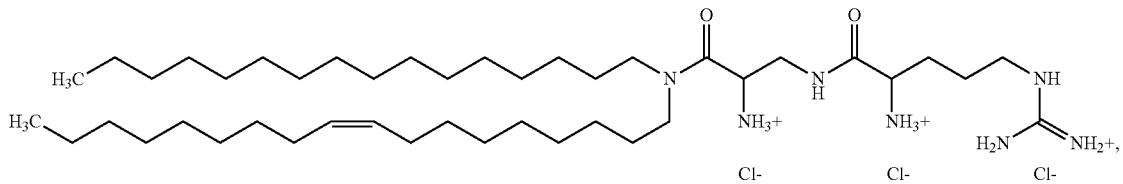
β-arginyl-2,3-diamino propionic acid-N-palmityl-N-oleyl-amide trihydrochloride

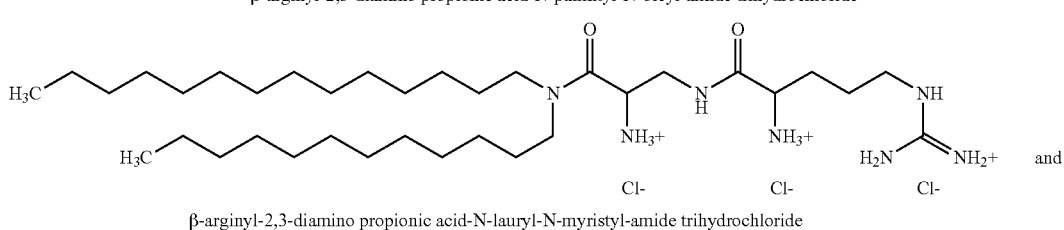
β-arginyl-2,3-diamino propionic acid-N-lauryl-N-myristyl-amide trihydrochloride -continued

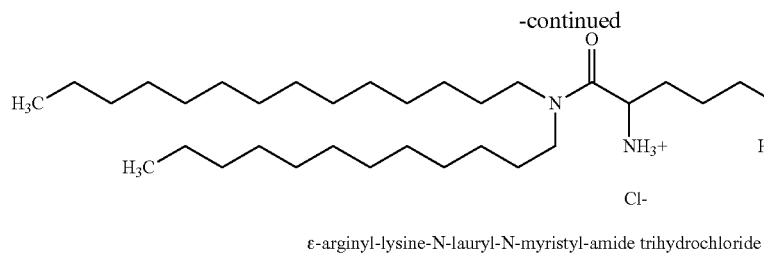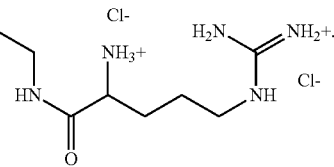

ε-arginyl-lysine-N-lauryl-N-myristyl-amide trihydrochloride

37. The lipid composition according to claim 1, further comprising a pharmaceutically acceptable carrier.

38. A pharmaceutical composition comprising a lipid composition according to claim 1 and a pharmaceutically active compound.

39. A method of introducing a pharmaceutically active compound into a cell comprising:
contacting the membrane of a cell with a composition according to claim 38, whereby said pharmaceutically active compound is transferred across said cell membrane into said cell.

40. The composition according to claim 38, wherein said pharmaceutically active compound is selected from the group consisting of a peptide, a protein, an oligonucleotide, a polynucleotide and a nucleic acid.

41. The composition according to claim 40, wherein said pharmaceutically active compound is an antibody.

42. The composition according to claim 40, wherein said pharmaceutically active compound is a nucleic acid selected from the group consisting of DNA, RNA, PNA and LNA.

43. The composition according claim 40, wherein said nucleic acid is a functional nucleic acid, and wherein the functional nucleic acid is selected from the group consisting of an RNAi, an siRNA, an siNA, an antisense nucleic acid, a ribozyme, an aptamer and a spiegelmer.

44. The composition according to claim 1, wherein the composition further comprises a second helper lipid, wherein said second helper lipid is from about 0.05 mol % to 4.9 mol % of the overall lipid content of the composition.

45. The composition according to claim 44, wherein the content of the second helper lipid is from about 1 to 2 mol % of the overall lipid content of the composition.

46. The composition according to claim 1, further comprising an RNAi, wherein the molar ratio of RNAi to cationic lipid component is from about 0 to about 0.075.

47. The composition according to claim 46, wherein the molar ratio of RNAi to cationic lipid component is from about 0.02 to about 0.05.

48. The composition according to claim 47, wherein the molar ratio of RNAi to cationic lipid component is about 0.037.

* * * * *

UNITED STATES PATENT AND TRADEMARK OFFICE
CERTIFICATE OF CORRECTION

PATENT NO. : 8,852,472 B2
APPLICATION NO. : 11/722948
DATED : October 7, 2014
INVENTOR(S) : Oliver Keil and Jörg Kaufmann Page 1 of 2

It is certified that error appears in the above-identified patent and that said Letters Patent is hereby corrected as shown below:

In the Specification

Column 4,
Line 13, "Y"" is a" should read --Y⁻ is a--.

Column 5,
Line 50, "a BEG" should read --a HEG--.

Column 7,
Line 2, "as further step:" should read --a further step:--.

Column 17,
Line 46, "of 99%" should read --of ≥ 99%--.

Column 20,
Line 61, "Schienk" should read --Schlenk--.

Column 21,
Line 15, "in 30 nil" should read --in 30 ml--.

Column 22,
Line 3, "Synthesis of ε-arginyl-lysine-N-laurel-N-myristyl" should read
    --Synthesis of ε-arginyl-lysine-N-lauryl-N-myristyl--.
Lines 6-7, "tetra-Boc-[ε-arginyl-lysin-N-laurly-N-myristyl amide]" should read
    --tetra-Boc-[ε-arginyl-lysine-N-lauryl-N-myristyl amide]--.
Line 16, "ε-arginyl-lysin-N-laurly-N-myristyl" should read
    --ε-arginyl-lysine-N-lauryl-N-myristyl--.
Line 17, "tihydrochloride." should read --trihydrochloride.--.
Line 49, "[##6]" should read --[#17]--.

Signed and Sealed this
Twelfth Day of May, 2015

Michelle K. Lee
*Director of the United States Patent and Trademark Office*

Column 23,
Line 6, "silicagel" should read --silica gel--.

Column 24,
Lines 55-56, "uaaguucuagcuguggugg-P (SEQ ID NO: 1);" should read
 --uaaguucuagcuguggugg-P (SEQ NO: 1);--.
Line 57, "ccaccacagcuagaacuua-P (SEQ ID NO: 2)," should read
 --ccaccacagcuagaacuua-P (SEQ ID NO: 2),--.

In the Claims

Column 28,
Line 60, Claim 8, "according to claim 3," should read --according to claim 4,--.

Column 29,
Line 3, Claim 10, "a MEG moiety," should read --a HEG moiety,--.